US012350471B2

United States Patent
Kitaguchi et al.

(10) Patent No.: US 12,350,471 B2
(45) Date of Patent: Jul. 8, 2025

(54) MEASUREMENT SYSTEM, MEASUREMENT METHOD, INJECTOR, AND METHOD FOR INJECTING BIOMOLECULE-CONTAINING SOLUTION INTO TO-BE-INJECTED CELL USING SAME

(71) Applicant: DAICEL CORPORATION, Osaka (JP)

(72) Inventors: Toru Kitaguchi, Tokyo (JP); Hiroshi Miyazaki, Tokyo (JP); Yuko Sakaguchi, Tokyo (JP)

(73) Assignee: Daicel Corporation, Osaka (JP)

( * ) Notice: Subject to any disclaimer, the term of this patent is extended or adjusted under 35 U.S.C. 154(b) by 1202 days.

(21) Appl. No.: 17/262,621

(22) PCT Filed: Jul. 25, 2019

(86) PCT No.: PCT/JP2019/029311
§ 371 (c)(1),
(2) Date: Jan. 22, 2021

(87) PCT Pub. No.: WO2020/022458
PCT Pub. Date: Jan. 30, 2020

(65) Prior Publication Data
US 2021/0268195 A1 Sep. 2, 2021

(30) Foreign Application Priority Data

Jul. 25, 2018 (JP) .................. 2018-139240
Oct. 26, 2018 (JP) .................. 2018-202114

(51) Int. Cl.
*A61M 5/30* (2006.01)
*G01N 21/359* (2014.01)

(52) U.S. Cl.
CPC ............. *A61M 5/30* (2013.01); *G01N 21/359* (2013.01)

(58) Field of Classification Search
CPC ............ A61M 5/30; A61M 2205/3306; A61M 2209/02; G01N 21/359; G01P 13/0006; G01P 5/26
See application file for complete search history.

(56) References Cited

U.S. PATENT DOCUMENTS

2005/0010168 A1  1/2005  Kendall
2005/0192530 A1* 9/2005  Castellano .............. A61M 5/30
                                                  604/70

(Continued)

FOREIGN PATENT DOCUMENTS

JP    H10-221357 A    8/1998
JP    2001-194379 A   7/2001

(Continued)

OTHER PUBLICATIONS

Supplementary Search Report dated Mar. 3, 2022 in corresponding European Application No. 19840022.8.

(Continued)

*Primary Examiner* — Tarun Sinha
(74) *Attorney, Agent, or Firm* — Knobbe Martens Olson & Bear LLP

(57) ABSTRACT

This application relates to a measurement system for measuring a behavior of an ejection liquid, which is ejected into an object from an ejection device, within the object. The system includes a container part formed of a resin material. The system also includes an imaging device disposed to image, across the object, a tip surface of the container part having an ejection port formed therein and being in contact with the object from a back side of the object in a predetermined state in which the ejection port is positioned from a front side of the object. The system further includes a first emission device that emits first near infrared light to the tip surface. In such a configuration, the behavior of the ejection (Continued)

liquid when the ejection liquid is ejected into the object from the ejection device can be imaged and measured by the imaging device.

10 Claims, 19 Drawing Sheets

(56) References Cited

U.S. PATENT DOCUMENTS

| | | | | |
|---|---|---|---|---|
| 2006/0173360 A1* | 8/2006 | Kalafut | ................ | A61B 5/0059 |
| | | | | 600/478 |
| 2018/0008513 A1* | 1/2018 | Iibuchi | ...................... | A61J 1/20 |

FOREIGN PATENT DOCUMENTS

| | | | |
|---|---|---|---|
| JP | 2004-358234 A | 12/2004 | |
| JP | 2017-064094 A | 4/2017 | |
| WO | WO 2006/074415 A2 | 7/2006 | |

OTHER PUBLICATIONS

Extended European Search Report dated Jun. 28, 2022 in European Application No. 19840022.8.

* cited by examiner (a)

(b)

(c)

(a)

(b)

MEASUREMENT SYSTEM, MEASUREMENT METHOD, INJECTOR, AND METHOD FOR INJECTING BIOMOLECULE-CONTAINING SOLUTION INTO TO-BE-INJECTED CELL USING SAME

The present application is a U.S. national phase application under 35 U.S.C. § 371 of International Application No. PCT/JP2019/029311, filed on Jul. 25, 2019, which claims the benefit of Japanese Patent Application Nos. 2018-139240 and 2018-202114 filed on Jul. 25, 2018 and Oct. 26, 2018, respectively, in the Japanese Patent Office, the entire disclosure of each of which is incorporated herein by reference.

TECHNICAL FIELD

The present invention relates to a measurement system for measuring the behavior of an ejection liquid ejected into an object from an ejection device and a measurement method thereof.

BACKGROUND ART

In the related art, as a method of directly observing a flow behavior of a fluid, various methods are used, which include, for example, a tuft method in which a direction of a flow is determined from a fluttering status of a plurality of short threads (tufts), an oil film method in which a mixture containing an oil and a pigment is applied to the surface of an object, and the state, direction, and velocity of a flow are determined from a streak pattern appearing due to the flow, a tracer method which is a method in which fine particles that move together with a fluid are mixed into the fluid, and movements thereof are tracked to observe the flow, and moreover as optical methods, a holographic method and a laser speckle method in addition to a Schlieren method using the change in refractive index based on the change in density (for example, refer to Patent Document 1). In addition, Patent Document 2 discloses a technology for easily analyzing the behavior of tracer particles in a captured image when the tracer method is used.

In addition, near infrared light may be used when the flow behavior of a fluid is observed. For example, Patent Document 3 discloses a technology in which near infrared light is used as a visualization tool for easily performing intravenous injection by making use of a characteristic of near infrared light being strongly absorbed on blood while the near infrared light has favorable living body permeability.

CITATION LIST

Patent Document

[Patent Document 1] Japanese Patent Application Publication No. 2001-194379

[Patent Document 2] Japanese Patent Application Publication No. H10-221357

[Patent Document 3] Japanese Patent Application Publication No. 2017-64094

[Patent Document 4] Japanese Patent Application Publication No. 2004-358234

[Patent Document 5] U.S. Patent Application Publication No. 2005/0010168 (Specification)

SUMMARY OF INVENTION

Technical Problem

A relatively high pressure is applied to a liquid to be ejected from an ejection device for liquid ejection. Therefore, the velocity of the ejection liquid immediately after ejection is relatively high, and it is not easy to measure the behavior thereof. In particular, when the ejection liquid is ejected into an object, in a case where the behavior of the ejection liquid is optically imaged and measured by an imaging device, the measurement becomes more difficult because the ejection liquid itself is present in the object.

Here, in view of the above problems, an object of the present invention is to provide a technology suitable for imaging and measuring by an imaging device the behavior of an ejection liquid when the ejection liquid is ejected into an object from an ejection device.

Solution to Problem

In order to address the above problem, the present invention provides a measurement system measuring a behavior of an ejection liquid, which is ejected into an object from an ejection device, within the object, the system including: a container part which includes a storage space, in which the ejection liquid is stored, and a flow path, through which the storage space communicates with an ejection port through which the ejection liquid is ejected to the outside, the container part being formed of a resin material; an imaging device which is disposed to be able to image, across the object, a tip surface of the container part having the ejection port formed therein and positioned with respect to the object from a back side of the object in a predetermined state in which the ejection port is positioned from a front side of the object, and a first emission device which emits first near infrared light to the tip surface.

The measurement system measures the behavior of the ejected ejection liquid when the ejection liquid stored in the storage space of the container part in the ejection device flows through the flow path and is ejected into the object from the ejection port. Here, the ejection device includes the container part and also a drive unit that applies energy for ejection to the ejection liquid stored in the storage space. For applying energy for ejection, a form of energy application by a known pressurization technique can be used. Regarding an example of energy to be applied, chemically generated energy, for example, combustion energy generated by an oxidation reaction of low explosive, high explosive, and the like may be exemplified. In addition, alternatively, the energy for pressurization may be electrically generated, and examples thereof include energy generated by a piezoelectric element or an electromagnetic actuator driven by input power. In addition, alternatively, the energy for pressurization may be physically generated, and examples thereof include elastic energy of an elastic component and internal energy of a compressed object such as a compressed gas. That is, the energy for pressurization may be any energy as long as it enables ejection of the ejection liquid in the ejection device. In addition, the energy for pressurization may be a composite type energy in which such combustion energy, electrical power energy, and internal energy such as elastic energy are appropriately combined.

In addition, regarding the ejection liquid, an appropriate liquid can be used according to the purpose of ejection from the ejection device. Here, a predetermined substance may be dissolved in the ejection liquid or may be simply incorporated without being dissolved in the liquid. As an example, when the ejection device is an injector, in consideration of the purpose of ejection, that is, the purpose of delivering a substance expected to exhibit a predetermined medical effect to a desired site of a living body or the like, vaccines for antibody enhancement, proteins for beauty, culture cells for hair regeneration, and the like may be exemplified as the predetermined substance, and these are contained in a liquid medium so that they can be ejected and thereby an ejection liquid is formed.

In addition, the container part is formed of a resin material, but as described above, any material that can reflect first near infrared light at the tip surface of the container part and allows second near infrared light to enter the container part can be appropriately used. For example, regarding the resin material, known nylon 6-12, polyarylate, polycarbonate, polybutylene terephthalate, polyphenylene sulfide, liquid crystal polymers, and the like can be used. In addition, these resin materials may contain a filling substance such as glass fibers and glass fillers, and polybutylene terephthalate may contain 20 to 80 mass % of glass fibers, polyphenylene sulfide may contain 20 to 80 mass % of glass fibers, and liquid crystal polymers may contain 20 to 80 mass % of minerals.

Here, in the ejection system, when the tip surface of the container part positioned with respect to the object, particularly, the tip surface including the ejection port, is imaged by the imaging device, the ejection device operates and the behavior of the ejection liquid ejected from the ejection port is measured. Regarding positioning of the container part with respect to the object, that is, the predetermined state, the tip surface of the container part may be in contact with the object, and when a certain inclusion is interposed between the tip surface and the object, the tip surface of the container part and the inclusion may be positioned to be in contact with each other and the inclusion and the object may be positioned to be in contact with each other. Here, the imaging device may directly image the tip surface of the container part or may perform imaging through a predetermined optical device (such as a mirror). In this case, since the tip surface of the container part is imaged by the imaging device across the object from the back side of the object, the thickness of the object is preferably set to a predetermined thickness that is thin enough that the ejection port can be determined. Thus, first near infrared light is emitted to the tip surface of the container part from the first emission device. As a result, the imaging device can suitably detect the ejection liquid ejected into the object on the captured image, and the measurement of the behavior of the ejection liquid is suitably realized.

Here, as an aspect of the first emission device, the first emission device is a device which emits the first near infrared light to the tip surface from the back side of the object, and an emission angle of the first near infrared light with respect to the tip surface may be set such that light reflected at the tip surface is directed toward the imaging device. In this aspect, since an emission angle of the first near infrared light is set such that reflected light of the first near infrared light at the tip surface is directed toward the imaging device, a situation in which the imaging device easily images the tip surface of the container part is formed. As a result, when emission of the first near infrared light by the first emission device is used, the imaging device can suitably detect the ejection liquid ejected into the object on the captured image, and the measurement of the behavior of the ejection liquid is suitably realized. In addition, since first near infrared light is emitted to the tip surface of the container part positioned with respect to the object in this aspect, regardless of the shape of the container part, particularly, the shape of a part near the flow path formed in the container part, the behavior of the ejection liquid can be measured.

In the above aspect, more preferably, a tip side reflective layer which reflects a part of the first near infrared light emitted from the back side of the object may be formed between the tip surface of the container part in the predetermined state and the object. In this manner, when the tip side reflective layer is disposed between the tip surface and the object, a larger amount of first near infrared light can be delivered to the imaging device, and thereby, more suitable measurement of the behavior of the ejection liquid is realized.

In addition, in the ejection system, the first emission device may be configured to emit the first near infrared light as pulsed light that blinks at a predetermined exposure time per frame for imaging by the imaging device. In this manner, when the first near infrared light is emitted as pulsed light, it is possible to shorten a time for which power is supplied to the light emitting element of the first emission device and minimize heat generation of the light emitting element. In other words, when a voltage several times higher than usual is applied to the light emitting element of the first emission device and pulsed light is emitted, the behavior of the ejection liquid can be measured with high brightness while suitably maintaining the operation of the light emitting element.

Here, in the measurement system described above, in consideration of the fact that there is an atmosphere around the container part when the first near infrared light is emitted from the back side of the object, in the image captured by the imaging device, an area corresponding to the tip surface of the container part may appear darker than the surrounding area (area corresponding to the atmosphere around the container part) because the amount of light is low. In particular, in the predetermined state, when the difference in refractive index between the object and the container part is smaller than the difference in refractive index between the object and the atmosphere, since the reflectance of the first near infrared light at the tip surface of the container part is relatively low, the area corresponding to the tip surface in the captured image tends to appear darker. When the area corresponding to the tip surface becomes dark in this manner, the contrast with the ejection liquid that is an imaging target becomes small, and it may be difficult to determine the behavior of the ejection liquid ejected from the ejection port of the tip surface.

Here, the measurement system may further include a second emission device which emits, from the front side of the object, second near infrared light that enters an outer peripheral surface of the container part, which is not in contact with the object in the predetermined state, and in which an angle of incidence of the second near infrared light on the outer peripheral surface is set such that the second near infrared light entering the container part passes through the container part and is directed toward the tip surface. The emitted second near infrared light is relatively unlikely to be reflected at the outer peripheral surface of the container part. Thus, when an angle of incidence of the second near infrared light on the outer peripheral surface is set such that the second near infrared light passes through the container part and is directed toward the tip surface, in the image captured by the imaging device, it is possible to increase the amount of light of the area corresponding to the tip surface of the container part. Therefore, when emission of first near infrared light by the first emission device and emission of second near infrared light by the second emission device are combined, the contrast with the ejection liquid that is an imaging target can be increased, the imaging device can suitably detect the ejection liquid emitted to the object on the captured image, and the measurement of the behavior of the ejection liquid is suitably realized. Here, like the first emission device, the second emission device may be configured to emit the second near infrared light as pulsed light that blinks at a predetermined exposure time per frame for imaging by the imaging device. In addition, in this case, one of the first emission device and the second emission device may be a device configured to emit pulsed light, or both of them may be a device configured to emit pulsed light.

Here, in the measurement system, in the container part, in a predetermined area which is at least a part of the outer peripheral surface from a light entry position, at which the second near infrared light enters, to an end on the tip surface side, a reflective member which reflects the second near infrared light that has passed through the container part from the light entry position and has reached the predetermined area into the container part may be provided. In this manner, when the reflective member is provided in a predetermined area of the outer peripheral surface of the container part, the second near infrared light that travels in the container part can be reflected and directed toward the tip surface. This is very useful in cases in which, due to the convenience of designing the container part and convenience of disposing the second emission device, a part or all of the second near infrared light cannot travel directly in the container part from the light entry position toward the tip surface. That is, the reflective member can prevent a part or all of the second near infrared light traveling in the container part from being emitted from the container part to the atmosphere side in a predetermined area, and thereby, a larger amount of light is collected on the tip surface of the container part, the contrast with the ejection liquid that is an imaging target increases, and therefore a suitable captured image of the ejection liquid near the tip surface can be obtained.

In addition, as another aspect of the first emission device, the first emission device is a device which emits, from the front side of the object, the first near infrared light that enters an outer peripheral surface of the container part, which is not in contact with the object in the predetermined state, and in which an angle of incidence of the first near infrared light on the outer peripheral surface may be set such that the first near infrared light entering the container part passes through the container part and is directed toward the tip surface, and the light is emitted to the tip surface. In addition, in the container part, in a predetermined area which is at least a part of the outer peripheral surface from a light entry position, at which the first near infrared light enters, to an end on the tip surface side, an outer peripheral side reflective member which reflects the first near infrared light that has passed through the container part from the light entry position and has reached the predetermined area into the container part may be provided. In such an aspect also, the first near infrared light may be emitted as pulsed light that blinks at a predetermined exposure time.

In addition, the invention of the present application can provide a method of measuring a behavior of an ejection liquid, which is ejected into an object from an ejection device, within the object. The method includes preparing an ejection device in which a container part is mounted, which includes a storage space, in which the ejection liquid is stored, and a flow path, through which the storage space communicates with an ejection port through which the ejection liquid is ejected to the outside, the container part being formed of a resin material; disposing an imaging device to be able to image, across the object, a tip surface of the container part having the ejection port formed therein and positioned with respect to the object from a backside of the object in a predetermined state in which the ejection port is positioned from a front side of the object; emitting first near infrared light from a first emission device to the tip surface; and imaging the ejection liquid ejected from the ejection device by the imaging device when the first near infrared light is emitted by the first emission device. Preferably, in the first emission device, an emission angle of the first near infrared light with respect to the tip surface from the back side of the object is set such that light reflected at the tip surface is directed toward the imaging device. In addition, the measurement method may further include emitting the second near infrared light to the outer peripheral surface from a second emission device in which an angle of incidence of second near infrared light from the front side of the object with respect to the outer peripheral surface of the container part that is not in contact with the object in the predetermined state is set such that the second near infrared light entering the container part passes through the container part and is directed toward the tip surface; and imaging the ejection liquid ejected from the ejection device by the imaging device in a case where the first near infrared light is emitted by the first emission device and the second near infrared light is emitted by the second emission device.

In addition, alternatively, the first emission device may be a device that emits, from the front side of the object, the first near infrared light that enters the outer peripheral surface of the container part, which is not in contact with the object in the predetermined state, and in which an angle of incidence of the first near infrared light on the outer peripheral surface may be set such that the first near infrared light entering the container part passes through the container part and is directed toward the tip surface, and the light is emitted to the tip surface.

Here, the technical idea disclosed with regard to the measurement system can also be applied to the invention of the measurement method as long as no technical discrepancy occurs.

Advantageous Effects of Invention

The behavior of the ejection liquid when the ejection liquid is ejected into the object from the ejection device can be imaged and measured by the imaging device.

BRIEF DESCRIPTION OF DRAWINGS

FIG. 4A and FIG. 4B are diagrams showing a progress state of near infrared light toward a tip surface of the container part when near infrared light is emitted as shown in FIG. 3.

FIG. 5A, FIG. 5B and FIG. 5C show captured images of the tip surface of the container part captured from the back side with an object therebetween by a high speed camera.

FIG. 15-1 is a graph showing the relationship between the displacement x of a tip of a solution containing biomolecules in an injection target and the velocity u(x) at the tip of the solution according to one embodiment of the present invention.

FIG. 15-2 is a graph showing the relationship between the displacement x of a tip of a solution containing biomolecules in an injection target and the velocity u(x) at the tip of the solution according to one embodiment of the present invention.

FIG. 15-3 is a graph showing the relationship between the displacement x of a tip of a solution containing biomolecules in an injection target and the velocity u(x) at the tip of the solution according to one embodiment of the present invention.

FIG. 17-1 is a diagram showing the distribution of cell nuclei in an individual mammal (living body) and DNA injected into the individual mammal (living body) according to one embodiment of the present invention (photograph annotated with drawing).

FIG. 17-2 is a diagram showing the distribution of cell nuclei in an individual mammal (living body) and DNA injected into the individual mammal (living body) according to one embodiment of the present invention (photograph annotated with drawing).

FIG. 17-3 is a diagram showing the distribution of cell nuclei in an individual mammal (living body) and DNA injected into the individual mammal (living body) according to a comparative example of the present invention (photograph annotated with drawing).

FIG. 17-4 is a diagram showing tissue damage due to injection of a DNA solution in an individual mammal (living body) according to one embodiment of the present invention (photograph annotated with drawing).

FIG. 17-5 is a diagram showing tissue damage due to injection of a DNA solution in an individual mammal (living body) according to one embodiment of the present invention (photograph annotated with drawing).

FIG. 17-6 is a diagram showing tissue damage due to injection of a DNA solution in an individual mammal (living body) according to one embodiment of the present invention (photograph annotated with drawing).

DESCRIPTION OF EMBODIMENTS

First Embodiment

A measurement system for measuring a behavior of an ejection liquid ejected from an ejection device and a measurement method thereof according to the present embodiment will be described below with reference to the drawings. Here, in the present embodiment, regarding the ejection device, a needleless injector (hereinafter simply referred to as an "injector") 1 that ejects an injection liquid (ejection liquid) into an object without using an injection needle is used. The injector 1 ejects an injection liquid into an object using combustion energy of an explosive. Here, in the present embodiment, the terms "tip side" and "base side" are used to represent a relative positional relationship in the injector 1 in the longitudinal direction. The "tip side" represents a position closer to the tip of the injector 1, that is, closer to an ejection port 31*a*. The "base side" represents a side opposite to the "tip side" in the longitudinal direction of the injector 1, that is, a side on the side of a drive unit 7. In addition, the configuration of the following embodiment is an example, and the configuration of the measurement system is not limited to the configuration of this embodiment.

<Configuration of Injector 1>

Figure 1:
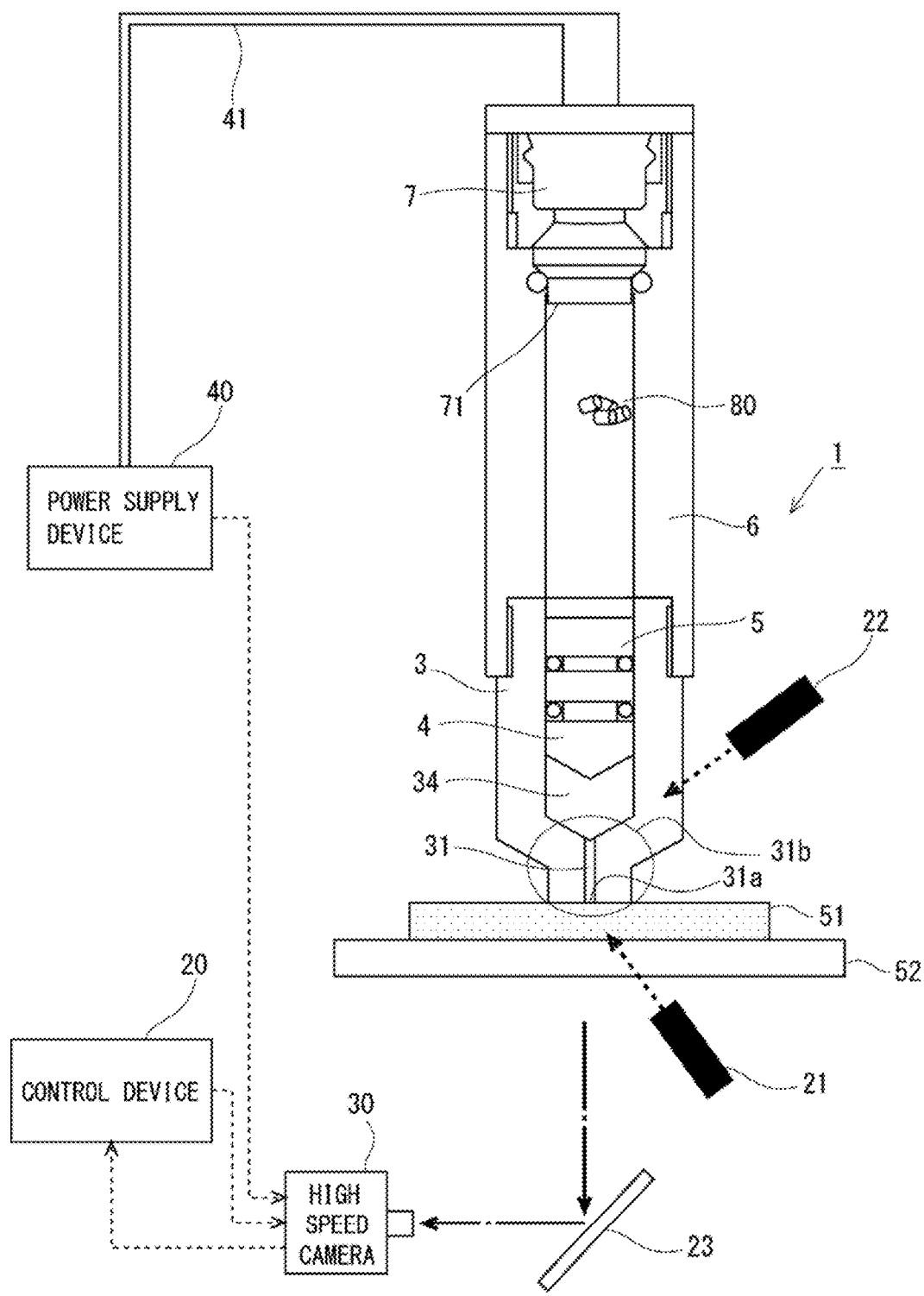
FIG. 1 is a first diagram showing a schematic configuration of a measurement system.

Here, FIG. 1 is a diagram showing the entire measurement system together with a schematic configuration of the injector 1. In FIG. 1, the cross-sectional state of the injector 1 in the longitudinal direction is shown. Here, when the measurement system measures a behavior of an injection liquid, the injection liquid to be ejected does not necessarily have to be an injection liquid when the injector 1 is actually used (for example, a liquid formed by incorporating a predetermined substance that exhibits the efficacy and function expected for an object in a liquid medium), and may be a liquid for imaging that is easily imaged by a high speed camera 30, which is an imaging device. In the present embodiment, such a liquid for imaging is also used as one form of an injection liquid.

The injector 1 has a configuration in which a container part 3 is mounted on the tip side of an injector main body 6 and the drive unit 7 is mounted on the base side. Here, the container part 3 includes a storage space 34 that is a space formed along the central axis of the main body of the container part 3 and in which an injection liquid can be stored and a flow path 31 that communicates with the storage space 34 and opens on the tip side, and is made of a resin. More specifically, a nozzle part 31*b* including the flow path 31 is formed on the tip side of the container part 3, and an end surface on the tip side of the nozzle part 31*b* is a tip surface 32 (refer to FIG. 2 and FIG. 3 to be described below). Therefore, the nozzle part 31*b* is a part of the container part 3 that does not include the storage space 34. Here, the opening of the flow path 31 becomes the ejection port 31*a*. Regarding a resin material that forms the container part 3 including the nozzle part 31*b*, for example, known nylon 6-12, polyarylate, polycarbonate, polybutylene terephthalate, polyphenylene sulfide, a liquid crystal polymer, or the like can be used. In addition, these resin materials may contain a filling substance such as glass fibers and glass fillers, and polybutylene terephthalate may contain 20 to 80 mass % of glass fibers, polyphenylene sulfide may contain 20 to 80 mass % of glass fibers, and the liquid crystal polymer may contain 20 to 80 mass % of minerals.

Here, in the storage space 34 of the container part 3, a plunger 4 is disposed so that it can slide in the direction (tip side direction) of the flow path 31, and a part or all of the storage space 34 formed between the plunger 4 and the main body of the container part 3 is a space in which an injection liquid is actually enclosed. Here, when the plunger 4 slides in the storage space 34, an injection liquid stored in the storage space 34 is pressed and ejected through the ejection port 31a provided on the tip side of the flow path 31. Therefore, the plunger 4 is made of a material that allows smooth sliding in the storage space 34 and prevents an injection liquid from leaking from the side of the plunger 4. Regarding a specific material of the plunger 4, for example, butyl rubber or silicon rubber can be used. In addition, styrene elastomers, hydrogenated styrene elastomers, and those obtained by mixing polyolefins such as polyethylene, polypropylene, polybutene, and an α-olefin copolymer, an oil such as liquid paraffin and a process oil, or a powdered inorganic material such as talc, cast, and mica thereto may be exemplified. In addition, polyvinyl chloride elastomers, olefin elastomers, polyester elastomers, polyamide elastomers, polyurethane elastomers and various rubber materials (particularly vulcanized) such as and natural rubber, isoprene rubber, chloroprene rubber, nitrile-butadiene rubber, and styrene-butadiene rubber, and mixtures thereof can be used as the material of the plunger 4. In addition, in order to secure and adjust slidability between the plunger 4 and the container part 3, the surface of the plunger 4 and the surface of the storage space 34 of the container part 3 may be coated and surface-treated with various substances. As the coating agent, PTFE (polytetrafluoroethylene), silicon oil, diamond-like carbon, nanodiamond, and the like can be used.

Here, the contour on the tip side of the plunger 4 has a shape that substantially matches the contour of the inner wall surface of a part connecting the storage space 34 to the flow path 31. Thereby, the plunger 4 slides when an injection liquid is ejected, and when the plunger 4 reaches the deepest position that is the innermost position in the storage space 34, the gap formed between the plunger 4 and the inner wall surface of the connecting part can be made as small as possible, and it is possible to prevent the injection liquid from remaining in the storage space 34 and being wasted.

Here, description will return to the container part 3. The inner diameter of the flow path 31 of the container part 3 is formed to be smaller than the inner diameter of the storage space 34. In such a configuration, the injection liquid pressurized to a high pressure is ejected from the ejection port 31a of the flow path 31 to the outside. In addition, a screw part for connecting the injector main body 6 to the container part 3 is formed in a part positioned on the base side of the container part 3.

In addition, a piston 5 is disposed in the container part 3 at a position adjacent to the plunger 4. The piston 5 is pressurized by a combustion product generated by an igniter 71 of the drive unit 7 and slides in the storage space 34. In addition, the piston 5 is made of a metal, and an O-ring, and the like may be disposed in a part thereof in order to improve adhesion with a sliding surface on which the piston 5 slides. Alternatively, the piston 5 may be made of a resin, and in this case, a metal may be used in combination with a part for which heat resistance and pressure resistance are required. The end surface on the base side of the piston 5 is exposed to the side of a through-hole formed inside the injector main body 6. The through-hole is a combustion chamber in which a combustion product generated by the igniter 71 of the drive unit 7 is released and a gas generating agent 80 combusted by the combustion product is disposed. Therefore, the end surface on the base side of the piston 5 receives a pressure from the combustion chamber, and the pressure is transmitted to the injection liquid stored in the storage space 34 via the plunger 4 for pressurization.

Next, the drive unit 7 will be described. The drive unit 7 has a main body formed in a tubular shape and includes the igniter 71 which is an electric igniter that combusts an ignition agent to generate energy for ejection, and is disposed in the injector main body 6 such that the igniter 71 faces the end surface of the base side so that the combustion energy from the igniter 71 is transmitted to the end surface on the base side of the piston 5. The main body of the drive unit 7 may be obtained by fixing an ejection-molded resin to a metal collar. A known method can be used for the ejection molding. Regarding a resin material of the main body of the drive unit 7, the same resin material as that of the container part 3 may be used.

Here, the combustion energy of the ignition agent used in the igniter 71 is energy for the injector 1 to eject the injection liquid to an object. Here, regarding the ignition agent, preferably, an explosive containing zirconium and potassium perchlorate (ZPP), an explosive containing titanium hydride and potassium perchlorate (THPP), an explosive containing titanium and potassium perchlorate (TiPP), an explosive containing aluminum and potassium perchlorate (APP), an explosive containing aluminum and bismuth oxide (ABO), an explosive containing aluminum and molybdenum oxide (AMO), an explosive containing aluminum and copper oxide (ACO), an explosive containing aluminum and iron oxide (AFO), or an explosive composed of a plurality of these explosives in combination may be exemplified. These explosives generate a plasma with a high temperature and a high pressure during combustion immediately after ignition, but when they reach room temperature, and the combustion product is condensed, they exhibit a characteristic that the generated pressure drops sharply because no gas component is contained. Other explosives may be used as the ignition agent as long as an injection liquid can be appropriately ejected.

In addition, in the injector 1, in order to adjust a transition of the pressure applied to the injection liquid via the piston 5, in addition to the ignition agent, the gas generating agent 80 that is combusted by the combustion product generated by combustion of the explosive by the igniter 71 to generate a gas is made to be disposed in the through-hole of the injector main body 6. The disposition location is a location that is exposed to the combustion product from the igniter 71. In addition, alternatively, the gas generating agent 80 may be disposed in the igniter 71 as disclosed in WO 01-031282, Japanese Patent Application Publication No. 2003-25950, and the like. As an example of the gas generating agent, a single-base smokeless explosive composed of 98 mass % of nitrocellulose, 0.8 mass % of diphenylamine, and 1.2 mass % of potassium sulfate may be exemplified. In addition, various gas generating agents used in a gas generating device for airbags and a gas generating device for seatbelt pretensioners can be used. When the dimensions, size, and shape of the gas generating agent, and particularly, the shape of the surface thereof, when disposed in a through-hole 64 of the injector main body 6, are adjusted, it is possible to change the combustion completion time of the gas generating agent, and thereby, the transition of the pressure applied to the injection liquid can be adjusted and a desired transition of the ejection pressure can be made.

When DC power is supplied from a power supply device 40 to the drive unit 7 of the injector 1 configured in this manner, the igniter 71 operates to release a combustion product, and the gas generating agent 80 is combusted by the combustion product. As a result, the piston 5 is pressed and the injection liquid is pressurized via the plunger 4. The pressurized injection liquid is ejected from the ejection port 31*a* of the nozzle part 31*b*. Here, FIG. 1 shows a state in which the tip surface 32 of the nozzle part 31*b* in which the ejection port 31*a* is formed is in contact with and positioned with respect to an object 51 into which an injection liquid is ejected and the liquid can be ejected into the object 51 when the drive unit 7 operates. Here, the object 51 is an object to which an injection liquid whose behavior is measured by the measurement system of the present embodiment is ejected. For example, the object 51 can be the excised skin of a rat. In the present embodiment, the object 51 is formed to be relatively thin in order to measure the behavior of the injection liquid on the object 51. In addition, in the state shown in FIG. 1, in the state in which the object 51 is disposed on a colorless and transparent acrylic plate 52, the injector 1 is disposed thereon with the tip surface 32 of the nozzle part 31*b* positioned. In this manner, the side on which the injector 1 is disposed when the object 51 is used as a reference is defined as the front side of the object 51.

In addition, in the measurement system, at a position where the tip surface 32 of the nozzle part 31*b* can be imaged with the object 51 therebetween from the back side of the object 51 (that is, the side opposite to the front side on which the injector 1 is disposed), the high speed camera 30, which is an imaging device, is disposed. The high speed camera 30 is a camera that can image an event occurring in a very short time at a high speed of about several thousand to 10,000 frames per second. For example, it is preferable to perform imaging at a speed of at least 1,000 fps, preferably at least 5,000 fps, and more preferably at least 10,000 fps. Since the injection liquid ejected from the injector 1 diffuses in the object 51 in a very short time, such a high speed camera 30 is beneficial. Here, the high speed camera 30 may directly image the tip surface 32 or may be disposed so that it images the tip surface 32 via an optical device such as a mirror 23 as shown in FIG. 1. In addition, in the measurement system, a control device 20, which is a computer, is disposed, the control device 20 controls the power supply device 40 and the high speed camera 30, collects image data captured by the high speed camera 30, and executes a predetermined control program, and thus the measurement of the behavior of the injection liquid is realized through image processing of the collected image data or the like.

Here, in the measurement system, in order to supply an amount of light necessary for imaging to the tip surface 32 of the nozzle part 31*b* in the field of view of the high speed camera 30, a back side emission device 21 that emits near infrared light with a predetermined wavelength (in this case, corresponding to the first emission device of the present application) is disposed on the back side of the object 51. The back side emission device 21 is, for example, a laser emission device that can emit near infrared light of 850 nm. Then, the back side emission device 21 emits the near infrared light to the tip surface 32, and an emission angle is set with respect to the tip surface 32 from the back side emission device 21 so that light reflected at the tip surface 32 is directed toward the high speed camera 30 via the mirror 23. Here, the emission angle is an angle formed by a normal direction of the tip surface 32 and a direction in which the near infrared light is emitted. In this manner, if near infrared light is emitted from the back side emission device 21, when the high speed camera 30 faces the tip surface 32 with the object 51 therebetween, it is possible to image the behavior of the injection liquid in the object 51 (for example, how the injection liquid diffuses in the object 51) when the injector 1 operates.

However, in the disposition state of the injector 1 shown in FIG. 1, the tip surface 32 of the nozzle part 31*b* is in contact with the object 51, but there is an atmosphere on the side of the nozzle part 31*b*. Therefore, in the field of view from the high speed camera 30, an area corresponding to the tip surface 32 tends to appear relatively darker than an area corresponding to the surrounding atmosphere. This is because, since the refractive index of the object 51 is relatively closer to the refractive index of the container part 3 including the nozzle part 31*b* than the refractive index of atmosphere, a difference in the refractive index between the object 51 and the container part 3 is smaller than a difference in the refractive index between the object 51 and the atmosphere around the container part 3. As a result, even if near infrared light is emitted by the back side emission device 21, it is not sufficiently reflected by the tip surface 32, the amount of near infrared light escaping into the container part 3 through the tip surface 32 from the object 51 increases, and thus, it is difficult to obtain a sufficient amount of reflected light for imaging the behavior of the injection liquid at a high speed.

Here, in the measurement system of the present embodiment, in addition to the back side emission device 21, a front side emission device 22 (in this case, corresponding to a second emission device of the present application) is disposed. The front side emission device 22 is also a laser emission device that can emit near infrared light with a predetermined wavelength (for example, 850 nm). However, unlike the back side emission device 21, the front side emission device 22 is disposed on the front side of the object 51 and the near infrared light is emitted to the outer peripheral surface of the container part 3. Here, a first emission mode of near infrared light in the front side emission device 22 will be described with reference to FIG. 2. Here, in the container part 3 shown in FIG. 2, descriptions of the plunger 4, the piston 5, and the injection liquid are omitted.

Figure 2:
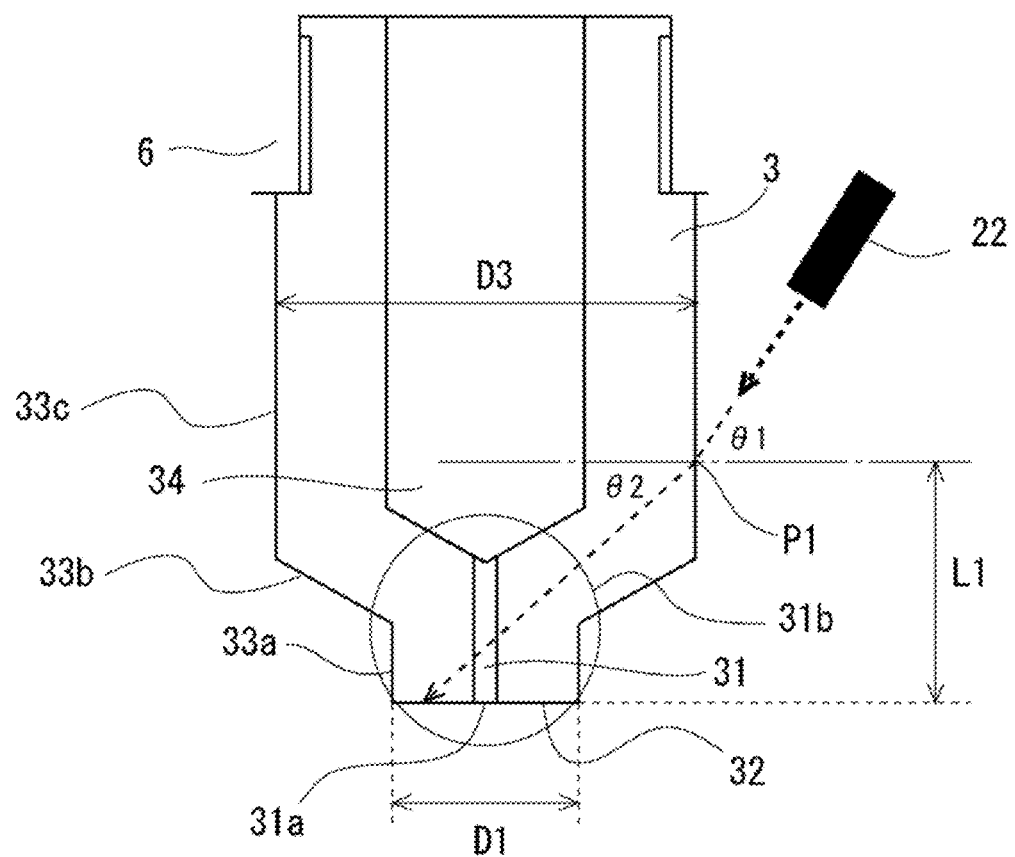
FIG. 2 is a diagram showing a configuration of a container part attached to an ejection device and showing a first mode in which near infrared light is emitted to the container part.

As shown in FIG. 2, in the container part 3, the nozzle part 31*b* is positioned on the tip side, the tip surface 32 is formed on the tip side, and the ejection port 31*a* is disposed therein. Thus, the flow path 31 is formed from the ejection port 31*a* along the central axis of the nozzle part 31*b*, and the storage space 34 is additionally connected thereto. Here, within the outer peripheral surface of the container part 3, the outer peripheral surface excluding the tip surface 32 in contact with the object 51 is the outer peripheral surface on the side of the container part 3, and as shown in FIG. 2, from the tip side, a first outer peripheral surface 33*a*, a second outer peripheral surface 33*b*, and a third outer peripheral surface 33*c* are formed. The first outer peripheral surface 33*a* is an outer peripheral surface adjacent to the tip surface 32 and is positioned closest to the tip surface 32 of the container part 3, and on the other hand, the third outer peripheral surface 33*c* is an outer peripheral surface positioned farthest from the tip surface 32 of the container part 3 and is adjacent to the injector main body 6. In addition, the diameter D3 of the container part 3 corresponding to the third outer peripheral surface 33*c* is larger than the diameter D1 of the container part 3 corresponding to the first outer peripheral surface 33a. Therefore, the second outer peripheral surface 33b connecting the first outer peripheral surface 33a to the third outer peripheral surface 33c is inclined with respect to the central axis of the container part 3 in the cross section shown in FIG. 2.

Here, near infrared light from the front side emission device 22 enters a point P1 on the third outer peripheral surface 33c, which is separated by a distance L1 in the axial direction of the container part 3 with respect to the tip surface 32. As shown in FIG. 2, an angle of incidence θ1 of near infrared light from the front side emission device 22 in this case is set so that near infrared light input at the point P1 is refracted at a refraction angle θ2 and travels in the container part 3, and reaches the tip surface 32 of the nozzle part 31b without change. That is, in consideration of geometric conditions of the container part 3 such as the diameter (diameter of the tip surface 32) D1 of the container part 3 corresponding to the first outer peripheral surface 33a, the diameter D3 of the container part 3 corresponding to the third outer peripheral surface 33c, and the distance L1 from the tip surface of the light entry point P1, and refraction of near infrared light that enters the container part 3 from the atmosphere, the angle of incidence θ1 is set so that the near infrared light reaches the tip surface 32. Here, the flow path 31 is formed in the nozzle part 31b of the container part 3, but since the diameter of the flow path is very small, the progress of near infrared light in the container part 3 is not prevented.

When the front side emission device 22 is set in this manner, near infrared light emitted from the front side emission device 22 is refracted at the light entry point P1, and travels through the member of the container part 3. Here, in the container part 3, a relatively large wall thickness is secured between the inner wall surface of the storage space 34 and the first outer peripheral surface 33a to the third outer peripheral surface 33c. Therefore, the near infrared light can travel through the member having the wall thickness and directly reach the tip surface 32. As a result, in the field of view from the high speed camera 30, a preferable amount of light for imaging by the high speed camera 30 can be supplied to an area corresponding to the tip surface 32, which tends to appear relatively darker than an area corresponding to the atmosphere. If emission of near infrared light from the back side emission device 21 described above is combined, when the high speed camera 30 faces the tip surface 32 with the object 51 therebetween, it is possible to suitably image the behavior of the ejected injection liquid in the object 51 (for example, how the injection liquid diffuses in the object 51).

Next, a second emission mode of near infrared light in the front side emission device 22 will be described with reference to FIG. 3. In the container part 3 shown in FIG. 3, a reflective member 35 is provided on the first outer peripheral surface 33a. Specifically, the reflective member 35 is a so-called aluminum foil, and is provided on the surface so that it closely covers the first outer peripheral surface 33a. Thus, in the second emission mode, when near infrared light ejected from the front side emission device 22 enters the container part 3 at the point P1, and is refracted at the point (refracted at a refraction angle θ2' with respect to an angle of incidence θ1'), it does not directly reach the tip surface 32 but reaches the first outer peripheral surface 33a. However, since the reflective member 35 is disposed on the first outer peripheral surface 33a, near infrared light that has reached the first outer peripheral surface 33a is reflected by the reflective member 35 without leaking to the outside of the container part 3, and can reach the tip surface 32 as a result. The angle of incidence θ1' when near infrared light from the front side emission device 22 follows such an optical path can also be said to be an angle of incidence "set so that near infrared light entering the container part 3 passes through the container part 3 and is directed toward the tip surface 32".

Figure 3:
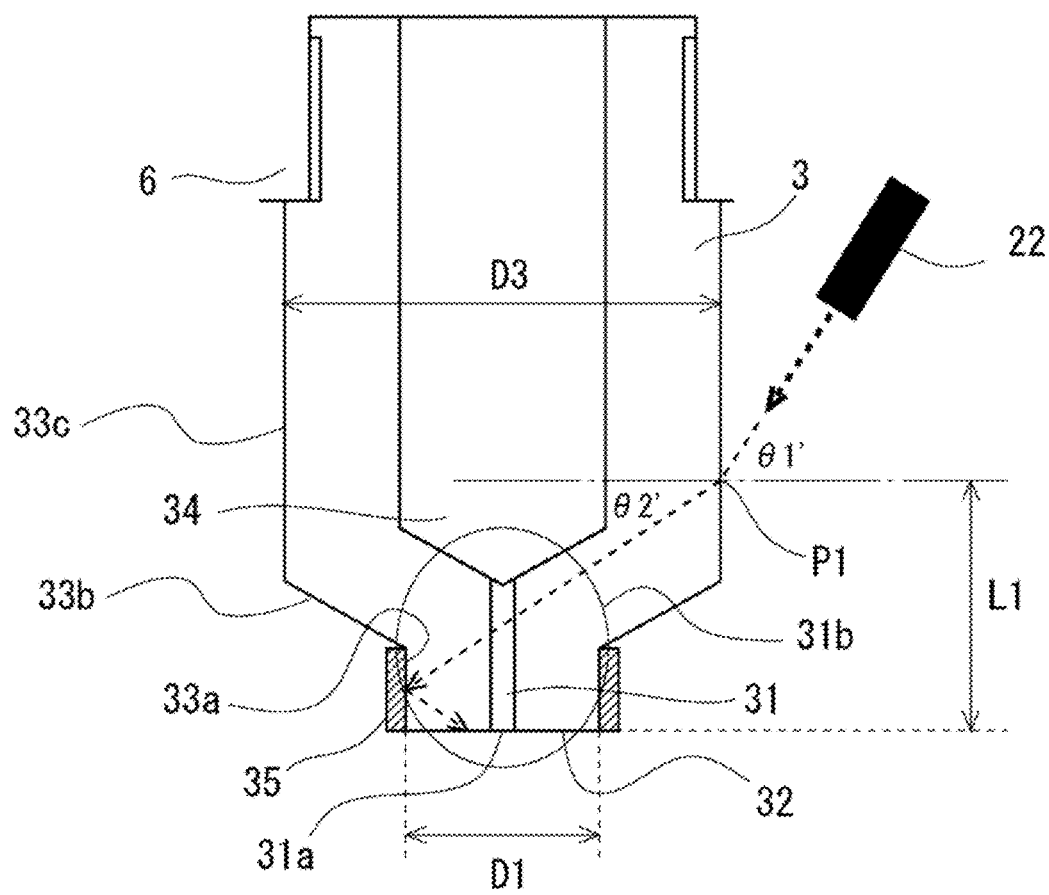
FIG. 3 is a diagram showing a configuration of the container part attached to the ejection device and showing a second mode in which near infrared light is emitted to the container part.

Here, when the injector 1 is fixed without disposing the object 51 in front of the tip surface 32 and near infrared light is emitted to the container part 3 from the front side emission device 22 as shown in FIG. 3, each status of the tip surface 32 when the reflective member 35 is attached (that is, the state shown in FIG. 3) and when the reflective member 35 is removed is shown in FIG. 4A and FIG. 4B. Specifically, FIG. 4A shows the status of the tip surface 32 when near infrared light is emitted from the front side emission device 22 while the reflective member 35 is attached as shown in FIG. 3, and FIG. 4B shows the status of the tip surface 32 when near infrared light is emitted from the front side emission device 22 while the reflective member 35 is removed.

As can be seen from FIG. 4A, as a result of reflection of near infrared light by the reflective member 35, a front area 321 of the tip surface 32 is brightened. On the other hand, when the reflective member 35 is removed, as shown in FIG. 4B, the brightness of the front area 321 of the tip surface 32 becomes darker than that of FIG. 4A. In addition, it can be seen that a relatively bright place 322 appears outside the front area 321. This is because, as shown in FIG. 3, when near infrared light refracted when light enters the container part 3 reaches the first outer peripheral surface 33a, since reflection by the reflective member 35 is not performed, the light directly moves outside the container part 3. It can be understood that, when the reflective member 35 is provided in this manner, the front area 321 of the tip surface 32 of the nozzle part 31b can be effectively brightened.

<Imaging Results>

Here, the results of imaging performed by the high speed camera 30 will be described with reference to FIG. 5A, FIG. 5B and FIG. 5C and FIG. 6. FIG. 5A, FIG. 5B and FIG. 5C show images captured by the high speed camera 30 corresponding to the following condition 1 to condition 3 when the injection liquid is not ejected by the injector 1.

Condition 1: emission of near infrared light only by the back side emission device 21

Condition 2: emission of near infrared light only by the front side emission device 22

Condition 3: emission of near infrared light by both the back side emission device 21 and the front side emission device 22

Figure 5:
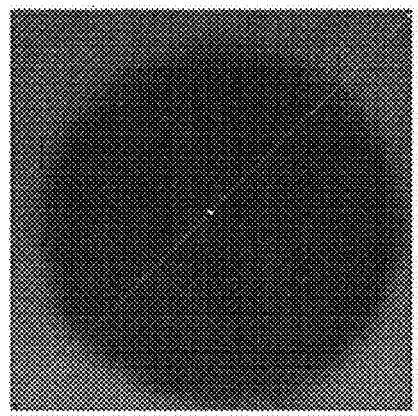
Figure 5:
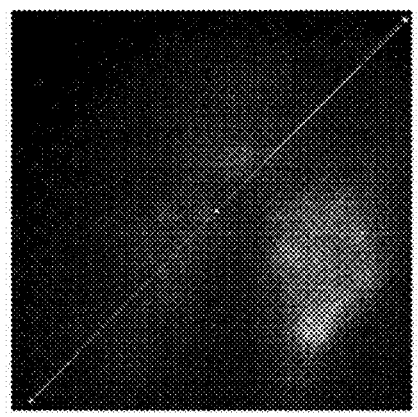
Figure 5:
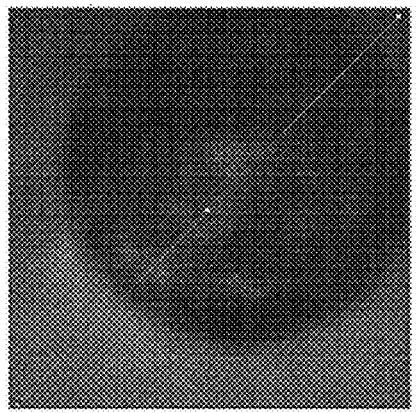
Figure 6:
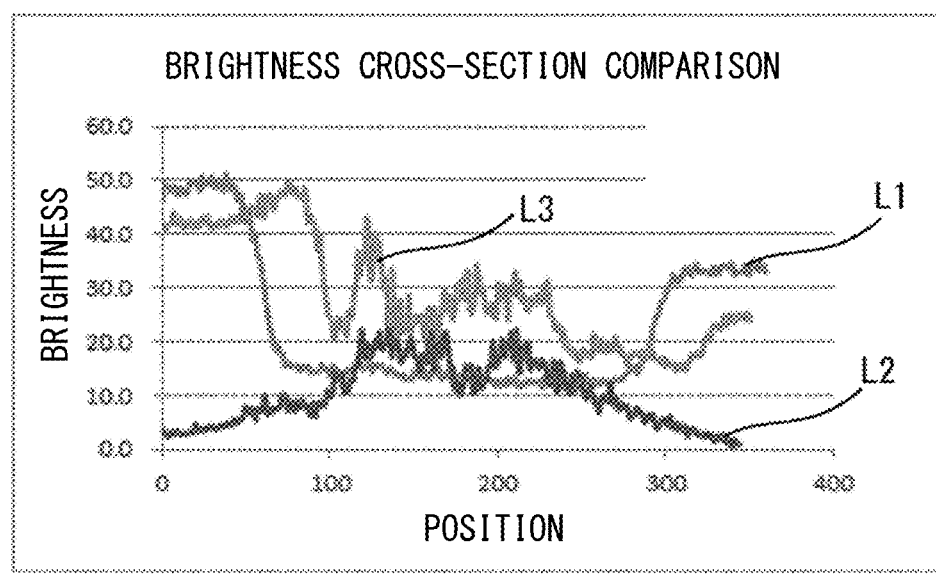
FIG. 6 is a graph obtained by analyzing the brightness on a captured image along the diagonal line of the captured image shown in FIG. 5A, FIG. 5B and FIG. 5C.

In addition, FIG. 6 shows the brightness of image pixels at the same place in each of the captured images in FIG. 5A, FIG. 5B and FIG. 5C (the place on the same white diagonal line in the captured image). The line L1 in FIG. 6 corresponds to FIG. 5A, the line L2 corresponds to FIG. 5B, and the line L3 corresponds to FIG. 5C.

Figure 7:
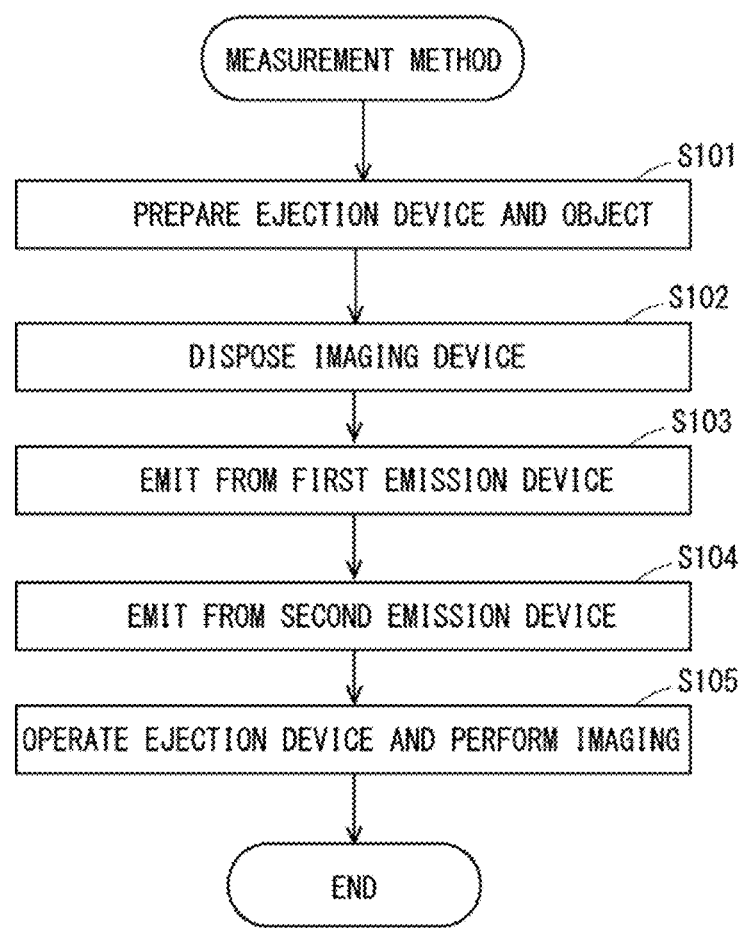
FIG. 7 is a flowchart showing a flow of a method of measuring a behavior of an ejection liquid in the measurement system.

In addition, the measurement of the behavior of the injection liquid by the high speed camera 30 is realized according to a flow of the measurement method shown in FIG. 7. First, in S101, the injector 1, which is an ejection device, performs setting so that the state shown in FIG. 1 is made. In this case, the tip surface 32 of the nozzle part 31b of the injector 1 comes in contact with the object 51 and it is preferable to perform fixing carefully so that the injector 1 is not displaced due to an impact generated when the injector 1 is operated. Subsequently, in S102, as shown in FIG. 1, the high speed camera 30 is disposed on the back side of the object 51 so that the tip surface 32 of the nozzle part 31b is within the field of view of the high speed camera 30. In this case, an optical device such as the mirror 23 may be disposed between the high speed camera 30 and the tip surface 32, and the optical device may be excluded.

Then, in S103, as described above, the back side emission device 21 is disposed on the back side of the object 51, and near infrared light is emitted therefrom toward the tip surface 32, and in addition, in S104, as shown in FIG. 2 and FIG. 3, the front side emission device 22 is disposed on the front side of the object 51 and emits near infrared light, and the near infrared light is caused to enter the container part 3 and travels in the container part 3 to the tip surface 32. The process of S105 is performed when near infrared light is emitted by the back side emission device 21 and the front side emission device 22. In S105, first, the control device 20 issues an instruction for waiting imaging to the high speed camera 30. The high speed camera 30 that has received the instruction is brought into a stand-by state in which imaging is possible immediately when a trigger signal comes from the outside. Then, in this state, when a user operates the power supply device 40, drive power is supplied to the drive unit 7 of the injector 1, and a trigger signal for the high speed camera 30 to perform imaging is transmitted from the power supply device 40. The high speed camera 30 that has received the trigger signal starts imaging and the imaging result is displayed on a monitor of the control device 20. In addition, the results of imaging performed by the high speed camera 30 are recorded in a recording device in the control device 20. Here, the processes of S102 to S104 may be performed in a different order or at the same time.

The captured image acquired by such a measurement method is an image captured according to the above condition 3. Here, when imaging is performed according to the condition 1 and condition 2, the flow of the measurement method is the same as shown in FIG. 7 except that near infrared light is emitted by an emission device in a condition different from the condition 3.

Here, in particular, the circular contour clearly seen in FIG. 5A and FIG. 5C corresponds to the outline of the tip surface 32 of the nozzle part 31b. In the case of the condition 1, as shown in FIG. 5A, an area corresponding to the tip surface 32 is very dark. This can also be understood from the line L1 in FIG. 6. This is because, when near infrared light is emitted only by the back side emission device 21 as described above, since the difference in refractive index between the object 51 and the nozzle part 31b (the container part 3) is relatively small, it is not easy to sufficiently generate reflected light from the near infrared light. However, this does not mean that the imaging mode according to the condition 1 is excluded from the category of the present application, but this point will be described in the following second embodiment.

On the other hand, in the case of the condition 3, as shown in FIG. 5C, an area corresponding to the tip surface 32 is brighter than that in the condition 1, which can also be understood from the line L3 in FIG. 6. As described above, this is because, when near infrared light is also emitted from the front side emission device 22 in addition to the back side emission device 21, near infrared light can reach the tip surface 32 from the inside of the container part 3. Therefore, if the injection liquid is ejected from the ejection port 31a, since the contrast with the injection liquid can be made relatively large, the presence of the injection liquid can be reliably detected. Here, in the condition 2, near infrared light is emitted only by the front side emission device 22, but when the line L2 in FIG. 6 is observed, although it is possible to recognize the rise in brightness transition centered on a position near 180, the brightness transitions relatively slowly, it is difficult to identify the outline (outmost position) of the ejected injection liquid. However, even in the imaging mode according to the condition 2, since the brightness rise near the center can be found as indicated by the line L2, this mode is also included in the category of the present application. Here, an imaging mode according to the condition 2 will be described in the following third embodiment.

Figure 8:
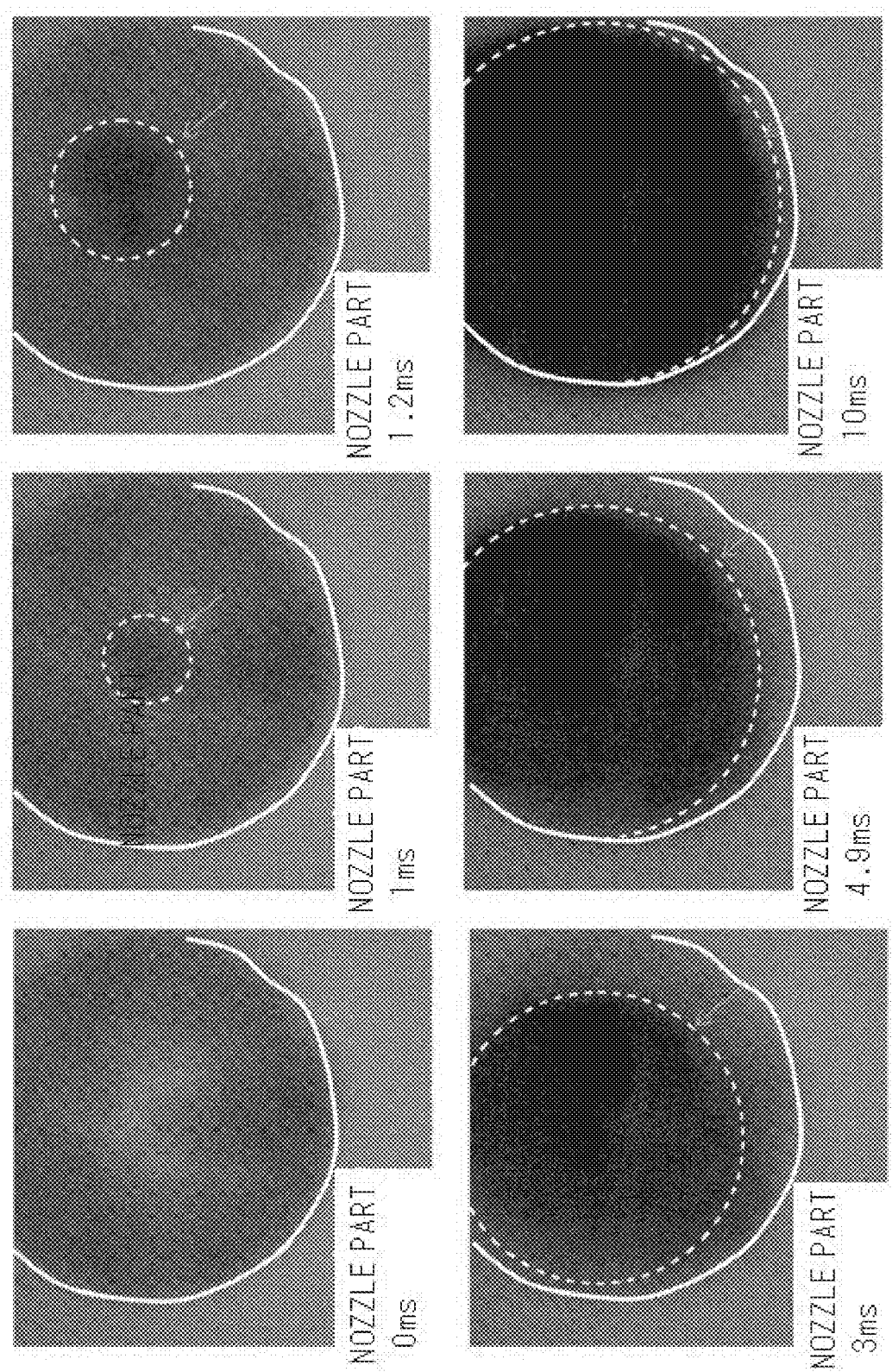
FIG. 8 shows captured images of the tip surface of the container part and a chemical solution that spreads in the object, which are captured in time series by a high speed camera when an ejection liquid is ejected by the ejection device.

Next, FIG. 8 shows images obtained by the high speed camera 30 by sequentially capturing the transition of diffusion of the injection liquid when the behavior of the injection liquid is measured according to the condition 3. In the images in FIG. 8, the time elapsed after the injector 1 is operated is shown. Specifically, images are captured by the high speed camera 30 when the elapsed time is 0 msec, 1 msec, 1.2 msec, 3 msec, 4.9 msec, and 10 msec. In the images, the white solid line indicates a contour line of the tip surface 32 of the nozzle part 31b. Here, in the images with an elapsed time other than 0 msec, the white dashed line indicates a contour line of the injection liquid that has been ejected and diffused in the object 51. In this manner, according to the measurement system of the present embodiment, it is possible to suitably measure the behavior of the ejected injection liquid occurring in a very short time. In particular, it can be understood that the presence of the injection liquid can be suitably detected at a timing immediately after the injector 1 is operated.

Second Embodiment

Figure 9:
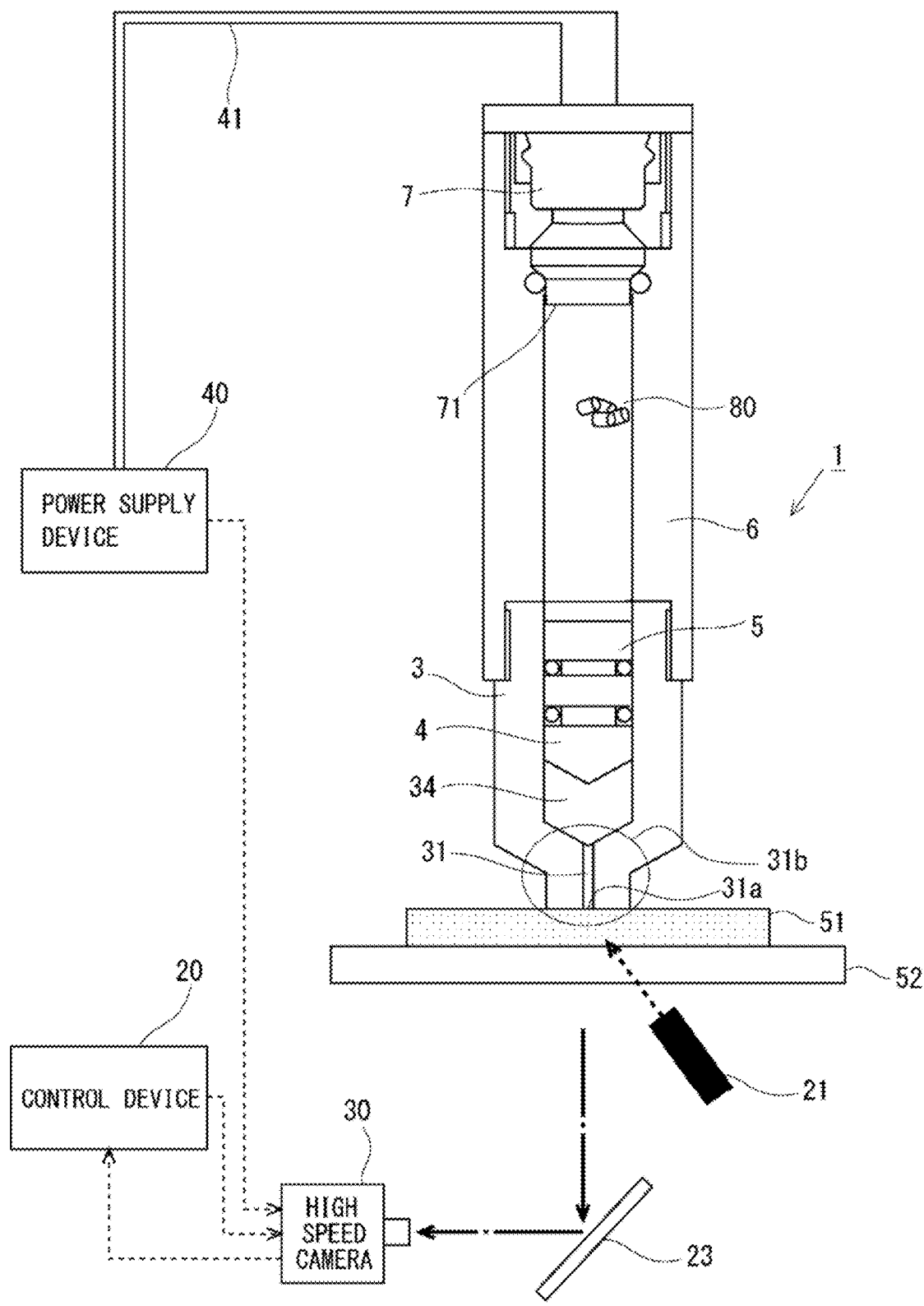
FIG. 9 is a second diagram showing a schematic configuration of the measurement system.

Next, the second embodiment of the measurement system will be described with reference to FIG. 9. Regarding the emission device, the measurement system shown in FIG. 9 has basically the same configuration as the measurement system shown in FIG. 1 except that the front side emission device 22 is not included but only the back side emission device 21 is included in the configuration. In this case, the back side emission device 21 corresponds to a first emission device of the present application. In such a configuration, when a sufficient amount of reflected light from the tip surface 32 of the nozzle part 31b is obtained, the behavior of the injection liquid ejected from the ejection port 31a can be sufficiently detected by the high speed camera 30. For example, the amount of reflected light from the tip surface 32 can be increased by appropriately selecting a material forming the container part 3 so that the difference in refractive index between the container part 3 including the nozzle part 31b and the object is relatively large.

In addition, in the measurement system configured in this manner, the behavior of the ejected injection liquid can be imaged if reflected light from the tip surface 32 is obtained. Therefore, regardless of the shape of the nozzle part 31b or the container part 3, the behavior of the injection liquid can be accurately determined. The same applies to the measurement system shown in the first embodiment described above.

Figure 10:
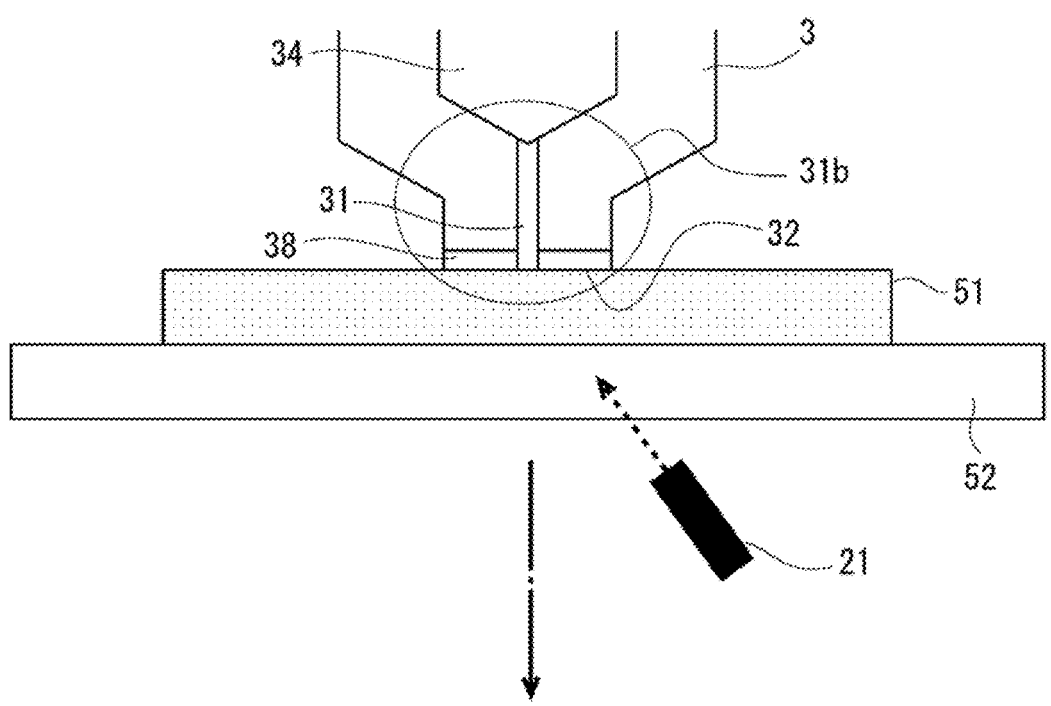
FIG. 10 is an enlarged view of an area near the tip of a nozzle part in a mode shown in FIG. 9.

In addition, as a modified example of the present embodiment, as shown in FIG. 10, a reflective layer 38 that reflects a part of near infrared light from the back side emission device 21 may be formed between the tip surface 32 of the nozzle part 31b and the object 51. Specifically, the reflective layer 38 is formed by applying a white paint (acrylic paint) to the tip surface 32 in a predetermined thickness. In such a configuration, the tip surface 32 of the nozzle part 31b is positioned with respect to the object 51 with the reflective layer 38 therebetween. In addition, alternatively, the reflective layer 38 may be formed by applying a white paint on the surface of the object 51 (surface with which the tip surface 32 comes in contact). That is, the reflective layer 38 may be interposed and disposed between the tip surface 32 of the nozzle part 31b and the surface of the object 51.

<Imaging Results>

Figure 11:
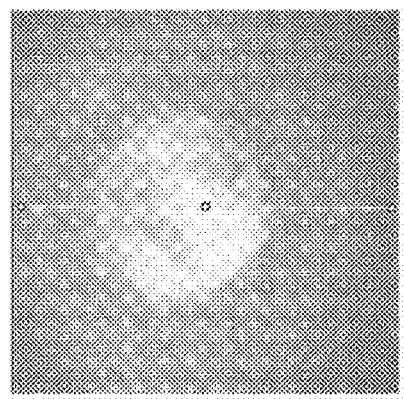
FIG. 11A and FIG. 11B show captured images of the tip surface of the container part captured from the back side with an object therebetween by a high speed camera in the mode shown in FIG. 9.
Figure 11:
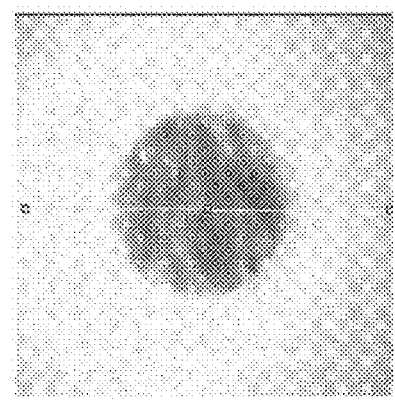

Here, the results of imaging performed by the high speed camera 30 in the present embodiment will be described with reference to FIG. 11A and FIG. 11B, and FIG. 12. FIG. 11A and FIG. 11B_show images captured by the high speed camera 30 corresponding to the following condition 11 to condition 12 when the injection liquid is not ejected by the injector 1.

Figure 12:
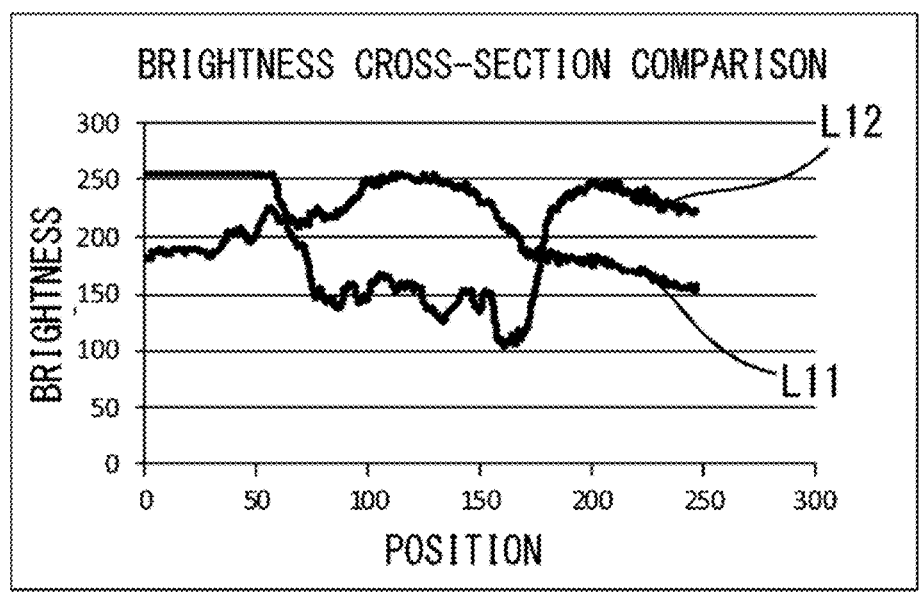
FIG. 12 is a graph obtained by analyzing the brightness on the captured image along the diagonal line of the captured image shown in FIG. 11A and FIG. 11B.

Condition 11: near infrared light is emitted only by the back side emission device 21 and the reflective layer 38 is formed Condition 12: near infrared light is emitted only by the back side emission device 21 and no reflective layer 38 is provided In addition, FIG. 12 shows the brightness of image pixels at the same place in each of the captured images in FIG. 11A and FIG. 11B (the place on the straight line in the captured image). The line L11 in FIG. 12 corresponds to FIG. 11A, and the line L12 corresponds to FIG. 11B. Here, the measurement of the behavior of the injection liquid by the high speed camera 30 is performed according to the flow of the measurement method shown in FIG. 7.

In the case of the condition 11, as shown in FIG. 11B, an area corresponding to the tip surface 32 is brighter than that in the case of the condition 12, which can be understood from the comparison between the line L11 and line L12 in FIG. 12. This is because a larger amount of near infrared light from the back side emission device 21 is reflected by the reflective layer 38, the contrast at the nozzle part 31 is improved, and as a result, the presence of the injection liquid can be reliably detected.

Third Embodiment

Figure 13:
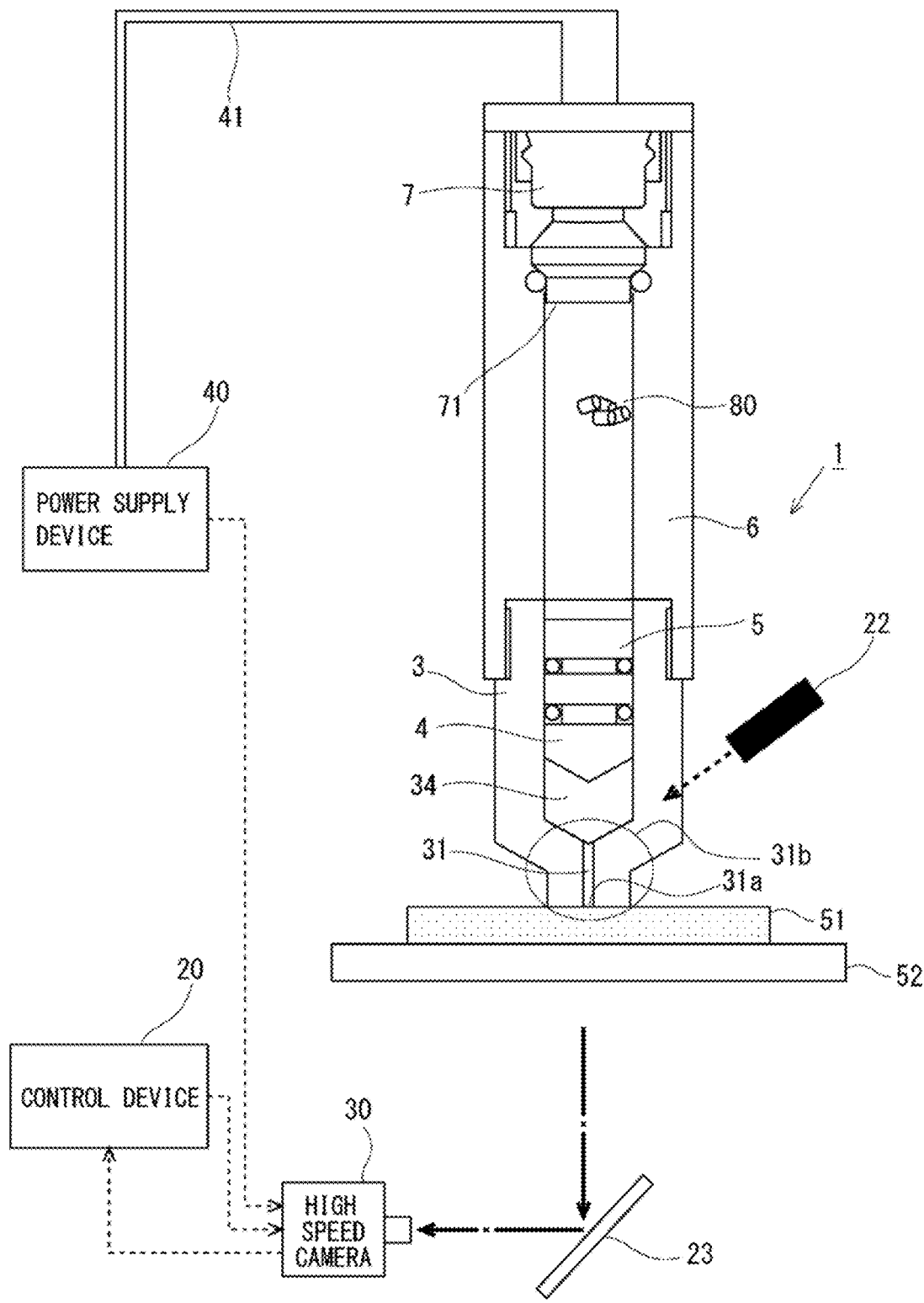
FIG. 13 is a third diagram showing a schematic configuration of the measurement system.

Next, the third embodiment of the measurement system will be described with reference to FIG. 13. Regarding the emission device, the measurement system shown in FIG. 13 has basically the same configuration as the measurement system shown in FIG. 1 except that the back side emission device 21 is not included but only the front side emission device 22 is included in the configuration. In this case, the front side emission device 22 corresponds to a first emission device of the present application.

In such a configuration, when a sufficient amount of near infrared light which is near infrared light emitted from the front side emission device 22 that has passed through the container part 3 and reached the tip surface 32 of the nozzle part 31b is obtained, the behavior of the injection liquid ejected from the ejection port 31a can be sufficiently detected by the high speed camera 30. Thus, preferably, when the reflective member 35 is provided on the first outer peripheral surface 33a of the container part 3 as shown in FIG. 3, the amount of near infrared light reaching the tip surface 32 can be increased to a degree suitable for measuring the behavior of the injection liquid.

Other Embodiments

In the above embodiments, the back side emission device 21 may emit near infrared light as pulsed light that blinks at a predetermined exposure time per frame of the high speed camera 30. The predetermined exposure time may be, for example, 10 usec, when the photographing speed of the high speed camera 30 is 10,000 fps (frame per second). When the back side emission device 21 emits near infrared light as pulsed light in this manner, it is possible to shorten a time for which power is supplied to the light emitting element of the back side emission device 21 and minimize heat generation of the light emitting element. In other words, even if the amount of power supplied to the light emitting element of the back side emission device 21 temporarily increases and the amount of light emitted when the pulse is turned ON increases, it is possible to maintain the state in which the light emitting element can operate suitably. As a result, it is possible to effectively increase the amount of reflected light from the tip surface 32 and thus it is possible to measure the behavior of the ejection liquid with higher brightness.

Next, the present application also discloses an invention of the following injector and a method of injecting a solution containing biomolecules into cells of an injection target using the same.

Regarding an injector for injecting a chemical solution into a living body or the like, in addition to a needle injector that performs injection through an injection needle and a needleless injector that performs injection without using an injection needle, there is a catheter including an injection needle and a drive source in order to transport a chemical solution to an injection target.

Among these, the needleless injector has a configuration in which an injection component is ejected by applying pressure with a pressurization gas, a spring, or an electromagnetic force to a storage chamber in which an injection liquid is stored. For example, a configuration in which a plurality of nozzle holes are formed in an injector main body and a piston that is driven during ejection is disposed corresponding to each nozzle hole may be used. In such a configuration, an injection liquid is simultaneously sprayed from a plurality of nozzle holes and uniform injection into a target is realized. Thus, a plasmid containing luciferase genes can be injected into rats and cells can be transferred with high efficiency.

In addition, there is a mode in which a pressurization gas is used as an ejection power source for an injection liquid in a needleless injector. For example, a pressurization mode in which high pressurization is instantly applied at the initial stage of ejection and then pressurization is gradually reduced over 40 to 50 msec may be exemplified.

On the other hand, when a conventional injector is used, tissues near the injection port for the injection target may be damaged. In addition, it has not been reported that a solution containing biomolecules can be directly injected into cells in a wide range of the injection target by an injector.

That is, the characteristic of the injector required to minimize damage to tissues near the injection port for the injection target has not been reported. In addition, there are no reports focusing on characteristics of an injector required for directly injecting a solution containing biomolecules into cells in a wide range of the injection target.

Here, the present application addresses a problem of provision of an injector that can minimize damage to tissues near the injection port for the injection target, and preferably, also discloses an invention that addresses a problem of provision of an injector that can directly inject a solution containing biomolecules into cells in a wide range of the injection target.

Based on the above, the inventors conducted extensive studies and as a result, found that, in an injector in which a solution containing biomolecules is stored, as a result focusing on k defined as an attenuation constant and $u_e$ defined as an asymptotic velocity when the relationship between the displacement x at the tip of the solution containing biomolecules in the injection target and the velocity u(x) at the tip of the solution is fitted using a least squares method by a fitting function represented by the following Formula (1), when the above k or $u_e$ is in a predetermined numerical value range, the above problem can be addressed, and completed the present invention.

$$u(x)=u_0 \exp(-kx)+u_e \quad (1)$$

(In Formula (1), $u_0$ represents a velocity coefficient (m/s), k represents a damping coefficient (1/mm), and $u_e$ represents an asymptotic velocity (m/s).)

The present invention is as follows.

[1] An injector injecting a solution containing biomolecules into an injection target without performing injection through a predetermined structure in a state, where the predetermined structure is inserted into the injection target, from an injector main body, the injector including a storage unit in which a solution containing biomolecules is stored; and a nozzle part having an ejection port through which the pressurized solution containing biomolecules flows and is ejected into the injection target, wherein when a relationship between displacement x at the tip of the solution containing biomolecules in the injection target and velocity u(x) at the tip of the solution is fitted using a least squares method by a fitting function represented by Formula (1) below, a damping coefficient k is at least 1.59.

$$u(x)=u_0 \exp(-kx)+u_e \quad (1)$$

(In Formula (1), $u_0$ represents a velocity coefficient (m/s), k represents a damping coefficient (1/mm), and $u_e$ represents an asymptotic velocity (m/s).)

[2] The injector according to [1], wherein the asymptotic velocity $u_e$ is at least 0.01.

[3] An injector injecting a solution containing biomolecules into an injection target without performing injection through a predetermined structure in a state where the predetermined structure is inserted into the injection target from an injector main body, the injector including a storage unit in which a solution containing biomolecules is stored; and a nozzle part having an ejection port through which the pressurized solution containing biomolecules flows and is ejected into the injection target, wherein when a relationship between displacement x at the tip of the solution containing biomolecules in the injection target and velocity u(x) at the tip of the solution is fitted using a least squares method by a fitting function represented by Formula (1) below, an asymptotic velocity $u_e$ is at least 0.01.

$$u(x)=u_0 \exp(-kx)+u_e \quad (1)$$

(In Formula (1), $u_0$ represents a velocity coefficient (m/s), k represents a damping coefficient (1/mm), and $u_e$ represents an asymptotic velocity (m/s).)

[4] A method of injecting a solution containing biomolecules into cells of an injection target using the injector according to any one of [1] to [3].

According to the present invention, it is possible to provide an injector that can minimize damage to tissues near the injection port for the injection target. Preferably, it is possible to provide an injector that can directly inject a solution containing biomolecules into cells in a wide range of the injection target.

As described above, the present invention includes an invention of an injector and an invention of a method of injecting a solution containing biomolecules into cells of an injection target using the injector, and details thereof will be described below.

<Invention of Injector>

One aspect of the injector of the present application is an injector injecting a solution containing biomolecules into an injection target without performing injection through a predetermined structure in a state, where the predetermined structure is inserted into the injection target, from an injector main body, the injector including a storage unit in which a solution containing biomolecules is stored; and a nozzle part having an ejection port through which the pressurized solution containing biomolecules flows and is ejected into the injection target, wherein when displacement x at the tip of the solution containing biomolecules in the injection target and velocity u(x) at the tip of the solution are fitted using a least squares method by a fitting function represented by Formula (1) below, a damping coefficient k is at least 1.59.

$$u(x)=u_0 \exp(-kx)+u_e \quad (1)$$

(In Formula (1), $u_0$ represents a velocity coefficient (m/s), k represents a damping coefficient (1/mm), and $u_e$ represents an asymptotic velocity (m/s).)

In the injector of the present application, when the relationship between the displacement x at the tip of the solution containing biomolecules in the injection target and the velocity u(x) at the tip of the solution is fitted using the least squares method by the fitting function represented by Formula (1), when the damping coefficient k is at least 1.59, it is possible to minimize damage to tissues near the injection port for the injection target.

The lower limit of the damping coefficient k is, in order of preference, at least 1.6, at least 1.8, and at least 2.0. In addition, the upper limit of the damping coefficient k is not particularly limited, but is generally not more than 10.0.

Specifically, the damping coefficient k is at least 1.59, and it is presumed that, as the attenuation constant k is larger, damage to tissues near the injection port for the injection target can be reduced. This is considered to be due to the following. That is, a large velocity u(0) at the tip of the solution (in other words, the velocity of the tip of the solution immediately after ejection) is necessary for forming pores in living tissues when the solution is injected into the living tissues. On the other hand, when the solution is injected at a high speed in the injection direction, and further spreads in the surrounding area with the injection direction as an axis, and intercellular substances in the surrounding area also spread, and damage the living tissues. Therefore, although a large velocity u(0) at the tip of the solution is preferable, it is preferable that $u_0\exp(-kx)$, which is the first term in Formula (1), sharply decrease as x is larger. That is, a larger damping coefficient k is preferable.

In the injector of the present application, when the relationship between the displacement x at the tip of the solution containing biomolecules in the injection target and the velocity u(x) at the tip of the solution is fitted using the least squares method by the fitting function represented by Formula (1), if the asymptotic velocity $u_e$ is preferably at least 0.01, the solution containing biomolecules can be directly injected into cells in a wide range of the injection target. In addition, the inside of cells herein is preferably the inside of cell nuclei.

The asymptotic velocity $u_e$ is preferably at least 0.01, more preferably at least 0.02, and on the other hand, preferably not more than 0.04. In addition, the upper limit of the asymptotic velocity $u_e$ is not particularly limited, and is generally not more than 0.1. Here, the velocity u(x) receives resistance in the injection target within the tissue. Therefore, it becomes 0 within a finite time, and becomes 0 within a finite displacement from the injection port.

Specifically, it is presumed that, when the asymptotic velocity $u_e$ is at least 0.01, the solution spreads in the surrounding area with the injection direction as an axis even after the first term in Formula (1) approaches zero due to contribution of the damping coefficient k, and the solution containing biomolecules can be directly injected into cells in a wide range of the injection target, and on the other hand, when the asymptotic velocity $u_e$ is not more than 0.04, excessive injection of the solution into weakly bound sites between cells and between tissues can be minimized and a rate of injection into cells can be increased.

In the present application, biomolecules injected into cells of the injection target are not particularly limited as long as they function in cells of the injection target and preferably, in cell nuclei, when injected into cells of the injection target. In addition, the biomolecule may be a natural substance or an artificially synthesized substance. Examples thereof include nucleic acids or derivatives thereof; nucleosides, nucleotides, or derivatives thereof; amino acids, peptides, proteins, or derivatives thereof; lipids or derivatives thereof; metal ions; low-molecular-weight compounds, or derivatives thereof; antibiotics; vitamins or derivatives thereof. As long as it is a nucleic acid, DNA or RNA may be used, and these may contain genes. In the following examples, free Cy3-labeled plasmid DNA is used as the biomolecule.

The form of biomolecules injected into cells of the injection target is not particularly limited, and for example, a free form, a form in which biomolecules are fixed to carriers such as nanoparticles, a modified form, or a form containing a solvent may be used as long as biomolecules are present stably, and there is no adverse effect such as destroying the injection target for injection or cells of the injection target.

When DNA contains genes, a design form in which the genes are contained in an expression cassette or an expression vector may be exemplified. In addition, for example, the gene may be disposed under control of a promoter suitable for the type of the injection target into which DNA is injected and the injection site. That is, in all of the forms, known genetic engineering techniques can be used.

In the injector of the present application, "tip side" means the side on which an ejection port from which a solution containing biomolecules is ejected from the injector is disposed, "base side" means the side opposite to the tip side in the injector, and these terms do not limitedly indicate a specific location or position.

The injector of the present application injects a solution containing biomolecules into an injection target without performing injection through a predetermined structure while the predetermined structure is inserted into the injection target from an injector main body. For example, an injector according to a first invention of the present invention may include, for example, a predetermined structure such as a catheter in order to guide the solution containing biomolecules from the injector main body to the injection target when the distance from the injector main body to the injection target is large. Therefore, the injector according to the first invention of the present invention may or may not such a predetermined structure, but when it includes the predetermined structure, it does not mean that a solution containing biomolecules is injected into the injection target while the predetermined structure is inserted into the injection target.

In the injector of the present application, a drive unit for pressurizing the solution containing biomolecules is not particularly limited. For example, pressurization may be performed with a pressure generated when the pressure of the compressed gas is released or performed with a pressure generated by combustion of an explosive ignited by an ignition device. In addition, pressurization using an electromagnetic force, for example, pressurization using a linear electromagnetic actuator may be used. Preferably, at least, a form using a pressure generated by combustion of an explosive ignited by an ignition device is used, or one or both of the above two pressurization modes may be used in combination.

When a form using a pressure generated by combustion of an explosive ignited by an ignition device for pressurization is used, regarding the explosive, for example, one of an explosive containing zirconium and potassium perchlorate (ZPP), an explosive containing titanium hydride and potassium perchlorate (THPP), an explosive containing titanium and potassium perchlorate (TiPP), an explosive containing aluminum and potassium perchlorate (APP), an explosive containing aluminum and bismuth oxide (ABO), an explosive containing aluminum and molybdenum oxide (AMO), an explosive containing aluminum and copper oxide (ACO), and an explosive containing aluminum and iron oxide (AFO) or an explosive composed of a plurality of these explosives in combination may be used. A characteristic of these explosives is that, even if the combustion product is a gas at a high temperature, it does not contain a gas component at room temperature, the combustion product is immediately condensed after ignition.

In addition, when the generated energy of the gas generating agent is used as ejection energy, regarding the gas generating agent, a single-base smokeless explosive and various gas generating agents used in a gas generating device for airbags and a gas generating device for seatbelt pretensioners can be used.

In the injector of the present application, the solution containing biomolecules may not be stored in the filling chamber from the beginning, but the solution containing biomolecules is sucked into the filling chamber through a nozzle having an ejection port and stored. In this manner, when a configuration in which an operation of performing filling into a filling chamber is used, it is possible to inject any required solution containing biomolecules into the injection target. Therefore, in the injector according to the first invention of the present invention, the syringe part is configured to be removable.

Regarding an example of the injector according to one embodiment of the first invention of the present invention, the injector 1 (needleless injector) will be described below with reference to the drawings. Here, the configuration of the following embodiment is an example, and the invention of the present invention is not limited to the configuration of this embodiment. Here, "tip side" and "base side" are used as terms representing the relative positional relationship in an injector 101 in the longitudinal direction. The "tip side" represents a position closer to the tip of the injector 101 to be described below, that is, a position closer to an ejection port 131*a*, and the "base side" represents a direction opposite to the "tip side" of the injector 1 in the longitudinal direction, that is, a direction on the side of a drive unit 107. In addition, in this example, a case in which combustion energy of an explosive ignited by an ignition device is used as ejection energy and a DNA solution is used as the solution containing biomolecules is exemplified, but the invention of the present invention is not limited thereto.

(Configuration of Injector 101)

Figure 14:
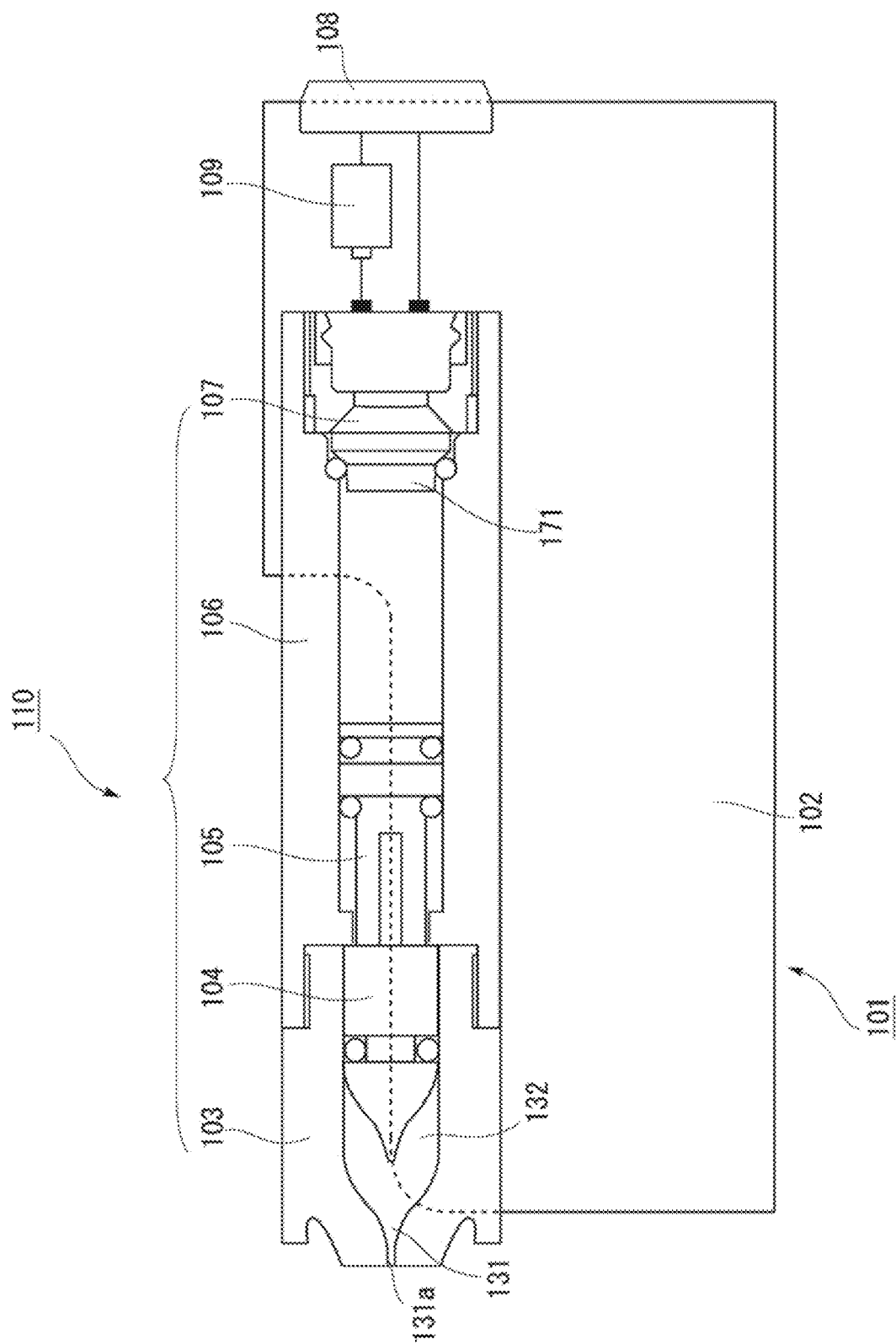
FIG. 14 is a diagram showing a schematic configuration of an injector according to one embodiment of the present invention.

FIG. 14 is a diagram showing a schematic configuration of the injector 101 and is a cross-sectional view of the injector 101 in the longitudinal direction. In the injector 101, an injector assembly 110 in which a sub-assembly including a syringe part 103 and a plunger 104 and a sub-assembly including an injector main body 106, a piston 105, and the drive unit 107 are integrally assembled is attached to a housing (injector housing) 102.

As described above, the injector assembly 110 is configured to be removable from the housing 102. A DNA solution is filled into a filling chamber 132 formed between the syringe part 103 and the plunger 104 included in the injector assembly 110, and the injector assembly 110 is a unit that can be disposed whenever the DNA solution is ejected. On the other hand, on the side of the housing 102, a battery 109 that supplies power to an igniter 171 included in the drive unit 107 of the injector assembly 110 is included. Power is supplied from the battery 109 between an electrode on the side of the housing 102 and an electrode on the side of the drive unit 107 of the injector assembly 110 via a wiring when the user performs an operation of pressing a button 108 provided at the housing 102. Here, regarding the electrode on the side of the housing 102 and the electrode on the side of the drive unit 107 of the injector assembly 110, the shape and position of both electrodes are designed so that they automatically come in contact with each other when the injector assembly 110 is attached to the housing 102. In addition, the housing 102 is a unit that can be repeatedly used as long as power that can be supplied to the drive unit 107 remains in the battery 109. Here, in the housing 102, when power of the battery 109 is exhausted, only the battery 109 is replaced, and the housing 102 may be used continuously.

In addition, in the injector main body 106 shown in FIG. 14, in particular, no additional explosive component is disposed, and in order to adjust transition of the pressure applied to the DNA solution via the piston 105, a gas generating agent that generates a gas by combustion with a combustion product generated by combustion of an explosive in the igniter 171 or the like can be disposed in the igniter 171 or in the through-hole of the injector main body 106. A configuration in which a gas generating agent is disposed in the igniter 171 is an already known technique as disclosed in WO 01-031282, Japanese Patent Application Publication No. 2003-25950, and the like. In addition, as an example of the gas generating agent, a single-base smokeless explosive composed of 98 mass % of nitrocellulose, 0.8 mass % of diphenylamine, and 1.2 mass % of potassium sulfate may be exemplified. In addition, various gas generating agents used in a gas generating device for airbags and a gas generating device for seatbelt pretensioners can be used. When the dimension, size, and shape of the gas generating agent, and particularly, the shape of the surface thereof, when disposed in the through-hole, are adjusted, it is possible to change the combustion completion time of the gas generating agent, and thereby, the transition of the pressure applied to the DNA solution can be a desired transition, that is, a transition in which the DNA solution can be appropriately injected into the injection target. In the present invention, the drive unit 107 also includes the gas generating agent used as necessary.

(Injection Target)

The injection target in the present application is not limited but it may be, for example, any of cells, cells in cell sheets, cells in tissues, cells in organs (organisms), cells in organ systems, and cells in individuals (living bodies). Regarding a preferable injection target, the injection target derived from mammals may be exemplified. Cells in individual mammals (living bodies) are more preferable, cells in the skin are still more preferable, and cells in at least one tissue selected from the group consisting of intradermal, subcutaneous and cutaneous muscles are yet more preferable. In this case, a method in which a solution containing biomolecules is ejected into the skin surface of an individual mammal (living body) from an injector and is injected into cells in at least one tissue selected from the group consisting of intradermal, subcutaneous and cutaneous muscles in the skin from the skin surface can be used.

In addition, the system for injecting a solution containing biomolecules into an injection target from an injector may be any of an in vitro system, an in vivo system, an ex vivo system, and the like.

In addition, mammals are not particularly limited, and examples thereof include humans, mice, rats, guinea pigs, hamsters, cows, goats, sheep, pigs, monkeys, dogs, and cats. In addition, depending on the injection target, subjects excluding humans may be exemplified as mammals.

(Method of Confirming that Solution Containing Biomolecules is Directly Injected into Cell Nuclei of Injection Target)

A method of confirming that a solution containing biomolecules is directly injected into cell nuclei of an injection target is not particularly limited, and a known biological method can be used. For example, a method in which biomolecules are labeled with a fluorescence in advance, and injected into cell nuclei of an injection target and then observed under a fluorescence microscope may be exemplified. In the following examples, Cy3-labled plasmid V7905 (commercially available from Mirus) is used as DNA directly injected into cell nuclei of cells in individual mammals (living body), and DAPI is used as a nuclear staining dye. For example, samples can be prepared by acquiring tissues immediately after DNA is injected and segmenting them. In this case, DAPI staining may be performed at the same time. Since a red fluorescence is emitted from a position at which Cy3-labled plasmid V7905 is injected and a blue fluorescence due to DAPI is emitted from a position on cell nuclei, the position at which a blue-purple fluorescence is emitted can be identified as a position of Cy3-labled plasmid V7905 directly injected into cell nuclei according to observation under a fluorescence microscope.

Another aspect of the injector of the present application is an injector injecting a solution containing biomolecules into an injection target without performing injection through a predetermined structure in a state, where the predetermined structure is inserted into the injection target, from an injector main body, the injector including a storage unit in which a solution containing biomolecules is stored; and a nozzle part having an ejection port through which the pressurized solution containing biomolecules flows and is ejected into the injection target, wherein when a relationship between displacement x at the tip of the solution containing biomolecules in the injection target and velocity u(x) at the tip of the solution is fitted using a least squares method by a fitting function represented by Formula (1) below, an asymptotic velocity $u_e$ is at least 0.01.

$$u(x) = u_0 \exp(-kx) + u_e \quad (1)$$

(In Formula (1), $u_0$ represents a velocity coefficient (m/s), k represents a damping coefficient (1/mm), and $u_e$ represents an asymptotic velocity (m/s).)

For the description of this aspect, the disclosure of the present application described above is used. That is, in order to measure the behavior (flow) of the solution containing biomolecules, the measurement system and measurement method described with reference to FIG. 1 to FIG. 13 can be applied.

<Invention of Method of Injecting Solution Containing Biomolecules into Cells of Injection Target Using Injector (Hereinafter Simply Referred to as "Invention of Injection Method")>

The present invention is a method of injecting a solution containing biomolecules into cells of an injection target using the above injector.

For an injector, an injection target, and a solution containing biomolecules in the invention of the injection method, the above description of the invention of the injector is used.

EXAMPLES

While the present invention will be described below in more detail with reference to examples, the present invention is not limited to the following examples as long as it does not depart from the scope and sprit thereof.
(Evaluation of Intradermal Diffusion Rate)

Example 1-1

Skin tissue removed from rats was prepared. 100 μL of an Indian ink was filled into an injector (nozzle diameter: diameter 0.1 mm) shown in FIG. 14, and the Indian ink was injected into the skin tissue with a pressure generated by combustion of an ignition agent. The displacement x at the tip of the Indian ink that spreads in the skin tissue and the velocity u(x) at the tip of the Indian ink were measured. In the measurement, the measurement system and measurement method described with reference to FIG. 1 to FIG. 13 were beneficial. In addition, 35 mg of an explosive containing zirconium and potassium perchlorate (ZPP) was used as the explosive, and 40 mg of a single-base smokeless explosive was used as the gas generating agent. For measurement, a high-speed camera (FASTCAM SA-Z commercially available from Photoron Limited) was used.

Example 1-2

The procedure was performed in the same manner as in Example 1-1 except that 55 mg of ZPP was used.

Comparative Example 1-1

Biojector 2000 (registered trademark, nozzle diameter: 0.12 mm, commercially available from Bioject Medical Technologies, Inc.) was used as a needleless injector, 100 μL of an Indian ink was filled, and the procedure was performed according to the instruction manual. Measurement was performed in the same manner as in Example 1-1.

Figures 1, 15:
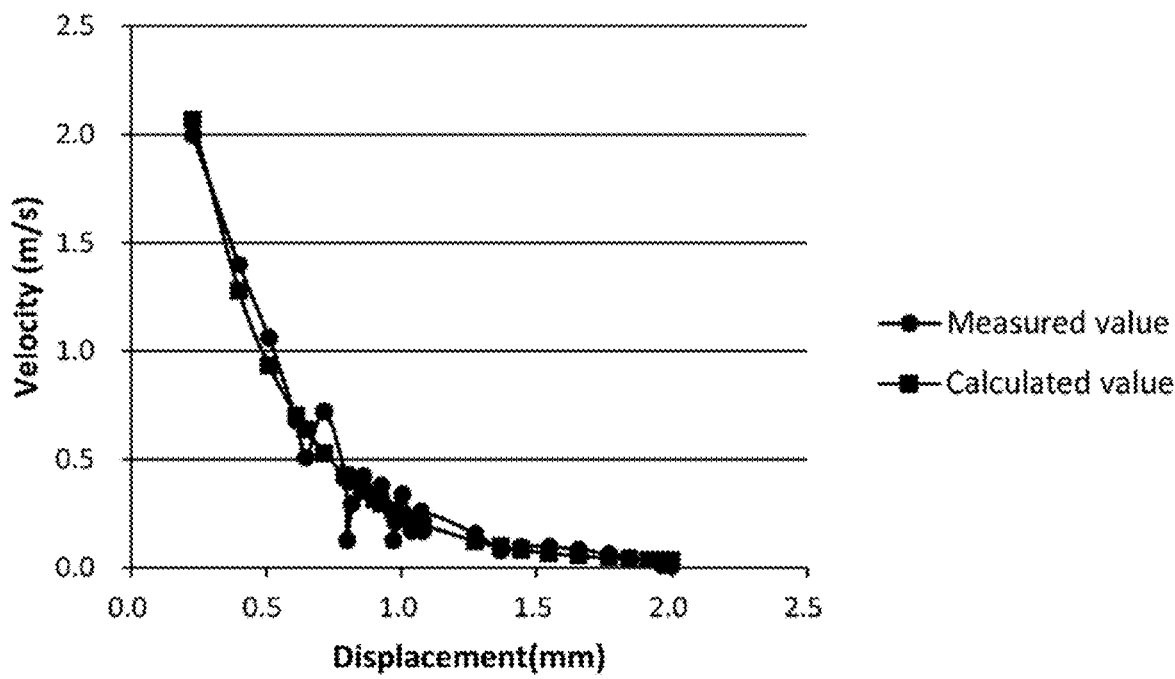
Figures 2, 15:
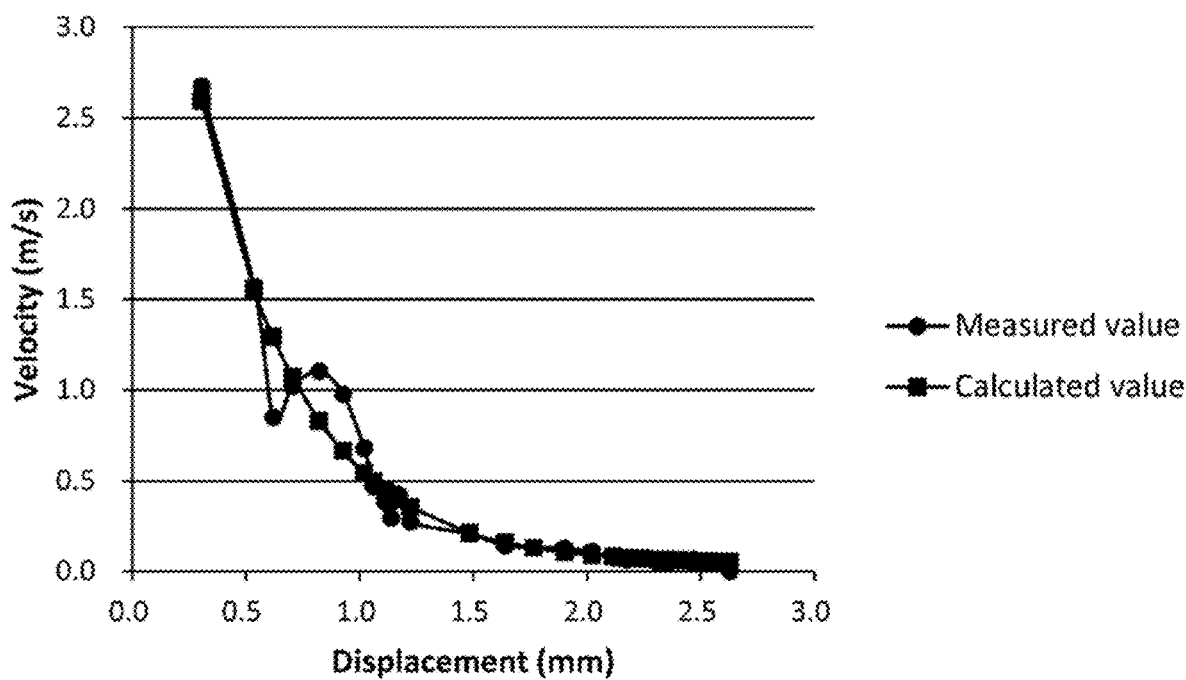
Figures 3, 15:
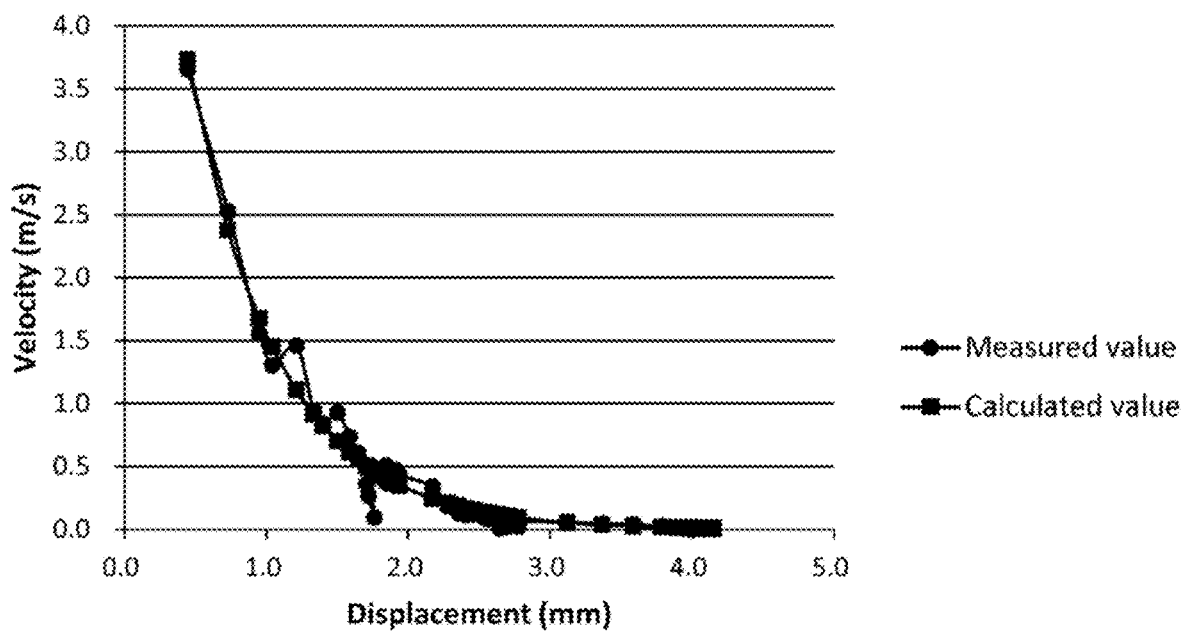

FIG. 15-1 and Table 1-1 are the graph and table showing the relationship between the displacement x at the tip of the Indian ink in the skin tissue and the velocity u(x) at the tip of the Indian ink in Example 1-1.

Here, in Table 1-1, the measured value (a) of the velocity at the tip of the Indian ink at a certain time was obtained by dividing the difference between the displacement of the Indian ink at the time described immediately before and the displacement of the Indian ink at the time described immediately after by the time. For example, in Table 1-1, the measured value in the column of a time of 0.9 ms was obtained by dividing the difference between the displacement of the Indian ink at a time of 0.8 ms and the displacement of the Indian ink at a time of 1.0 ms by the time of 0.2 ms. Here, the calculated value (b) was a numerical value used for fitting.

In addition, the times in Table 1-1 are listed from 0.8 ms, but the movement of the Indian ink in the injection target was observed only at 0.8 ms or later, and there is no meaning to the 0.8 ms itself.

TABLE 1-1

| Time (ms) | Displacement (mm) | Velocity (m/s) Measured value (a) | Velocity (m/s) Calculated value (b) | Displacement profile of normalized velocity (=(a)/$u_o$) |
|---|---|---|---|---|
| 0.8 | 0.00 | | | |
| 0.9 | 0.23 | 2.00 | 2.07 | 0.50 |
| 1.0 | 0.40 | 1.40 | 1.28 | 0.35 |
| 1.1 | 0.51 | 1.06 | 0.93 | 0.27 |
| 1.2 | 0.61 | 0.68 | 0.70 | 0.17 |
| 1.3 | 0.65 | 0.51 | 0.64 | 0.13 |
| 1.4 | 0.71 | 0.72 | 0.53 | 0.18 |
| 1.5 | 0.79 | 0.42 | 0.43 | 0.11 |
| 1.6 | 0.80 | 0.13 | 0.42 | 0.03 |
| 1.7 | 0.82 | 0.30 | 0.40 | 0.07 |
| 1.8 | 0.86 | 0.42 | 0.36 | 0.11 |
| 1.9 | 0.90 | 0.34 | 0.32 | 0.09 |
| 2.0 | 0.93 | 0.38 | 0.30 | 0.10 |
| 2.1 | 0.98 | 0.21 | 0.26 | 0.05 |
| 2.2 | 0.97 | 0.13 | 0.26 | 0.03 |
| 2.3 | 1.00 | 0.34 | 0.24 | 0.09 |
| 2.4 | 1.04 | 0.17 | 0.22 | 0.04 |
| 2.5 | 1.04 | 0.21 | 0.22 | 0.05 |
| 2.6 | 1.08 | 0.17 | 0.20 | 0.04 |
| 2.7 | 1.07 | 0.26 | 0.20 | 0.07 |
| 3.4 | 1.27 | 0.16 | 0.12 | 0.04 |
| 4.5 | 1.37 | 0.08 | 0.10 | 0.02 |
| 5.5 | 1.44 | 0.10 | 0.08 | 0.02 |
| 6.3 | 1.55 | 0.10 | 0.07 | 0.03 |
| 7.6 | 1.66 | 0.08 | 0.06 | 0.02 |
| 8.9 | 1.77 | 0.07 | 0.05 | 0.02 |
| 10.4 | 1.84 | 0.05 | 0.04 | 0.01 |
| 11.9 | 1.91 | 0.04 | 0.04 | 0.01 |
| 13.7 | 1.96 | 0.01 | 0.04 | 0.00 |
| 18.8 | 2.00 | 0.01 | 0.03 | 0.00 |

FIG. 15-2 and Table 1-2 are the graph and table showing the relationship between the displacement x at the tip of the Indian ink in the injection target and the velocity u(x) at the tip of the Indian ink in Example 1-2. Descriptions of the numerical values in Table 1-2 are the same as those already described in Table 1-1.

TABLE 1-2

| Time (ms) | Displacement (mm) | Velocity (m/s) Measured value (a) | Velocity (m/s) Calculated value (b) | Displacement profile of normalized velocity (=(a)/u$_o$) |
|---|---|---|---|---|
| 0.80 | 0.00 | | | |
| 0.90 | 0.31 | 2.68 | 2.59 | 0.52 |
| 1.00 | 0.54 | 1.57 | 1.56 | 0.31 |
| 1.10 | 0.62 | 0.85 | 1.29 | 0.17 |
| 1.20 | 0.71 | 1.02 | 1.07 | 0.20 |
| 1.30 | 0.82 | 1.10 | 0.83 | 0.22 |
| 1.40 | 0.93 | 0.98 | 0.66 | 0.19 |
| 1.50 | 1.02 | 0.68 | 0.55 | 0.13 |
| 1.60 | 1.06 | 0.47 | 0.50 | 0.09 |
| 1.70 | 1.11 | 0.38 | 0.45 | 0.07 |
| 1.80 | 1.14 | 0.30 | 0.43 | 0.06 |
| 1.90 | 1.17 | 0.42 | 0.40 | 0.08 |
| 2.00 | 1.22 | 0.28 | 0.36 | 0.05 |
| 3.00 | 1.49 | 0.21 | 0.21 | 0.04 |
| 4.00 | 1.64 | 0.14 | 0.16 | 0.03 |
| 5.00 | 1.77 | 0.13 | 0.13 | 0.03 |
| 6.00 | 1.90 | 0.13 | 0.11 | 0.02 |
| 7.00 | 2.02 | 0.11 | 0.09 | 0.02 |
| 8.00 | 2.12 | 0.08 | 0.08 | 0.01 |
| 9.00 | 2.17 | 0.06 | 0.07 | 0.01 |
| 10.00 | 2.24 | 0.07 | 0.07 | 0.01 |
| 11.00 | 2.31 | 0.06 | 0.06 | 0.01 |
| 12.00 | 2.35 | 0.05 | 0.06 | 0.01 |
| 13.00 | 2.41 | 0.06 | 0.06 | 0.01 |
| 14.00 | 2.47 | 0.06 | 0.06 | 0.01 |
| 15.00 | 2.54 | 0.06 | 0.05 | 0.01 |
| 16.00 | 2.58 | 0.04 | 0.05 | 0.01 |
| 17.00 | 2.63 | 0.02 | 0.05 | 0.00 |
| 18.00 | 2.63 | 0.00 | 0.05 | 0.00 |

FIG. 15-3 and Table 1-3 are the graph and table showing the relationship between the displacement x at the tip of the Indian ink in the injection target and the velocity u(x) at the tip of the Indian ink in Comparative Example 1-1. Descriptions of the numerical values in Table 1-3 are the same as those already described in Table 1-1.

TABLE 1-3

| Time (ms) | Displacement (mm) | Velocity (m/s) Measured value (a) | Velocity (m/s) Calculated value (b) | Displacement profile of normalized velocity (=(a)/u$_o$) |
|---|---|---|---|---|
| 0.8 | 0.00 | | | |
| 0.9 | 0.45 | 3.65 | 3.73 | 0.48 |
| 1.0 | 0.73 | 2.53 | 2.38 | 0.34 |
| 1.1 | 0.95 | 1.56 | 1.68 | 0.21 |
| 1.2 | 1.04 | 1.30 | 1.45 | 0.17 |
| 1.3 | 1.21 | 1.46 | 1.11 | 0.19 |
| 1.4 | 1.33 | 0.94 | 0.91 | 0.12 |
| 1.5 | 1.40 | 0.84 | 0.82 | 0.11 |
| 1.6 | 1.50 | 0.93 | 0.70 | 0.12 |
| 1.7 | 1.59 | 0.74 | 0.61 | 0.10 |
| 1.8 | 1.65 | 0.61 | 0.56 | 0.08 |
| 1.9 | 1.71 | 0.36 | 0.51 | 0.05 |
| 2.0 | 1.72 | 0.27 | 0.50 | 0.04 |
| 2.1 | 1.76 | 0.10 | 0.47 | 0.01 |
| 2.2 | 1.74 | 0.42 | 0.48 | 0.06 |
| 2.3 | 1.84 | 0.51 | 0.41 | 0.07 |
| 2.4 | 1.84 | 0.37 | 0.41 | 0.05 |
| 2.5 | 1.92 | 0.47 | 0.36 | 0.06 |
| 2.6 | 1.94 | 0.43 | 0.35 | 0.06 |
| 3.1 | 2.17 | 0.34 | 0.24 | 0.05 |
| 3.6 | 2.28 | 0.19 | 0.20 | 0.02 |
| 4.1 | 2.35 | 0.13 | 0.18 | 0.02 |

TABLE 1-3-continued

| Time (ms) | Displacement (mm) | Velocity (m/s) Measured value (a) | Velocity (m/s) Calculated value (b) | Displacement profile of normalized velocity (=(a)/u$_o$) |
|---|---|---|---|---|
| 4.6 | 2.41 | 0.11 | 0.17 | 0.02 |
| 5.1 | 2.47 | 0.12 | 0.15 | 0.02 |
| 5.6 | 2.53 | 0.10 | 0.14 | 0.01 |
| 6.1 | 2.57 | 0.08 | 0.13 | 0.01 |
| 6.6 | 2.61 | 0.08 | 0.12 | 0.01 |
| 7.6 | 2.69 | 0.02 | 0.11 | 0.00 |
| 8.6 | 2.64 | 0.01 | 0.12 | 0.00 |
| 9.6 | 2.71 | 0.07 | 0.10 | 0.01 |
| 10.6 | 2.78 | 0.03 | 0.09 | 0.00 |
| 11.6 | 2.76 | 0.06 | 0.10 | 0.01 |
| 16.6 | 3.12 | 0.06 | 0.05 | 0.01 |
| 21.6 | 3.37 | 0.05 | 0.04 | 0.01 |
| 26.6 | 3.58 | 0.04 | 0.03 | 0.01 |
| 31.6 | 3.78 | 0.03 | 0.02 | 0.00 |
| 36.6 | 3.85 | 0.02 | 0.02 | 0.00 |
| 41.6 | 3.93 | 0.01 | 0.01 | 0.00 |
| 46.6 | 3.95 | 0.01 | 0.01 | 0.00 |
| 56.6 | 4.08 | 0.01 | 0.01 | 0.00 |
| 66.6 | 4.07 | 0.00 | 0.01 | 0.00 |
| 76.6 | 4.00 | 0.00 | 0.01 | 0.00 |
| 86.6 | 4.09 | 0.01 | 0.01 | 0.00 |
| 96.6 | 4.15 | 0.01 | 0.01 | 0.00 |

Figure 16:
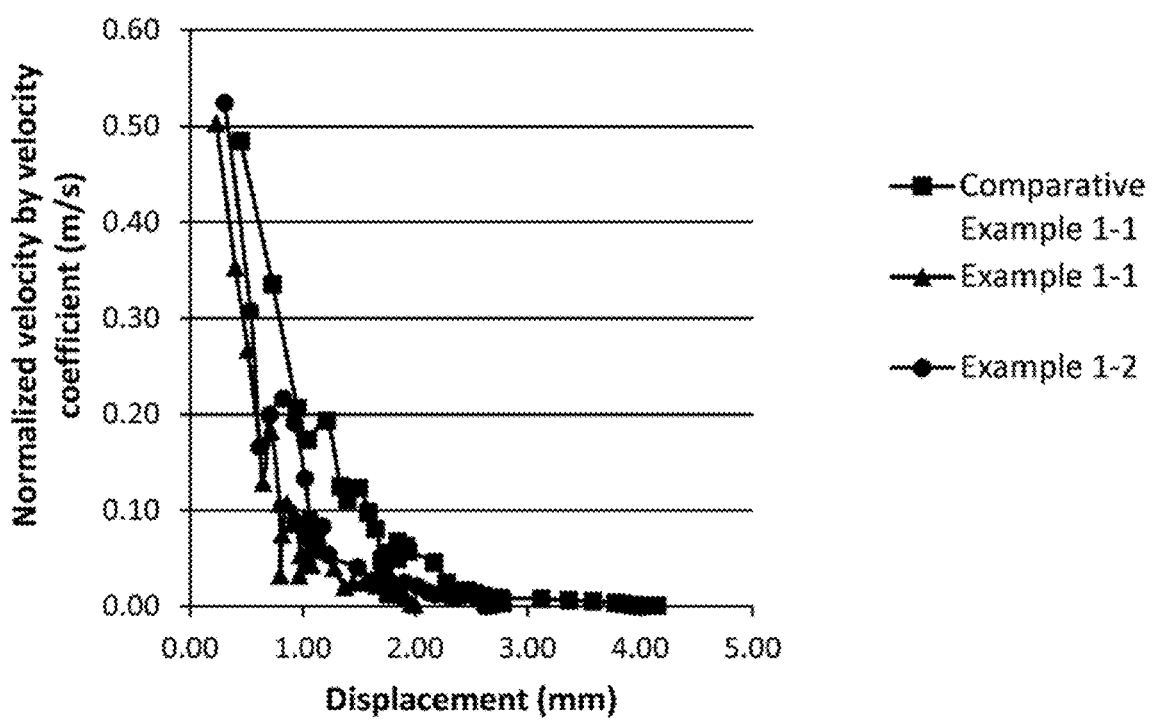
FIG. 16 is a graph showing the relationship between the displacement x of a tip of a solution containing biomolecules in an injection target and the velocity obtained by normalizing the velocity u(x) at the tip of the solution by a velocity coefficient u0 according to one embodiment of the present invention.

The graph in FIG. 16 was obtained by normalizing the results obtained in Example 1-1, Example 1-2, and Comparative Example 1-1 with a velocity coefficient $u_0$.

To summarize the results:
in Example 1-1, $u_0$=3.97, k=2.89, $u_e$=0.02;
in Example 1-2, $u_0$=5.11, k=2.26, $u_e$=0.04; and
in Comparative Example 1-1, $u_0$=7.54, k=1.58, $u_e$=0.00.

(Test in which DNA Solution is Injected into Cell Nuclei of Cells in Individual Mammal (Living Body))

Example 2-1

35 mg of an explosive containing zirconium and potassium perchlorate (ZPP) was used as the explosive, 40 mg of a single-base smokeless explosive was used as the gas generating agent, 30 μL of a solution containing Cy3-labled plasmid V7905 (solvent: endotoxin-free TE buffer), final concentration: 0.1 mg/mL) was filled into the injector used in Example 1-1, and the solution was injected into the skin on the back of female SD rats (10 weeks old).

Figures 1, 17:
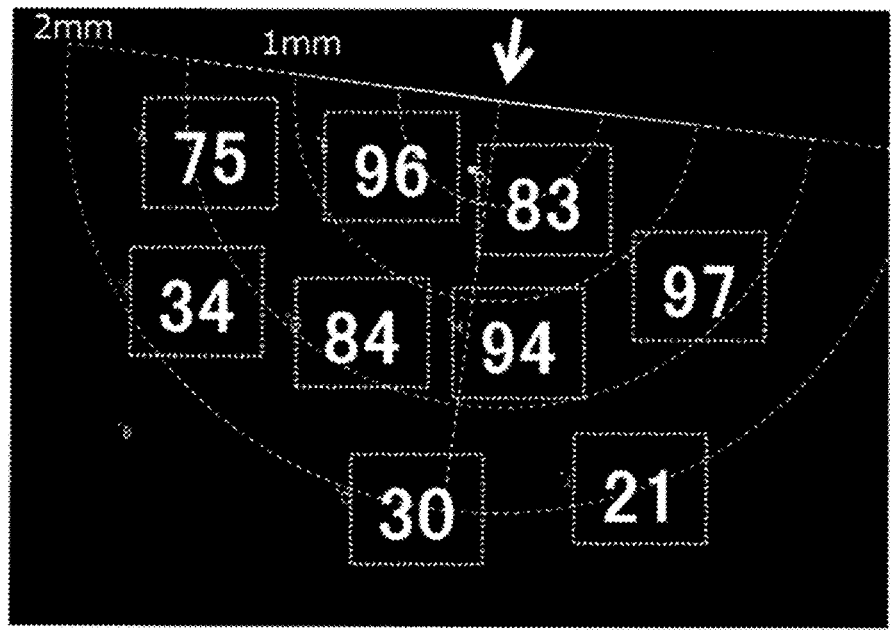
Figures 2, 17:
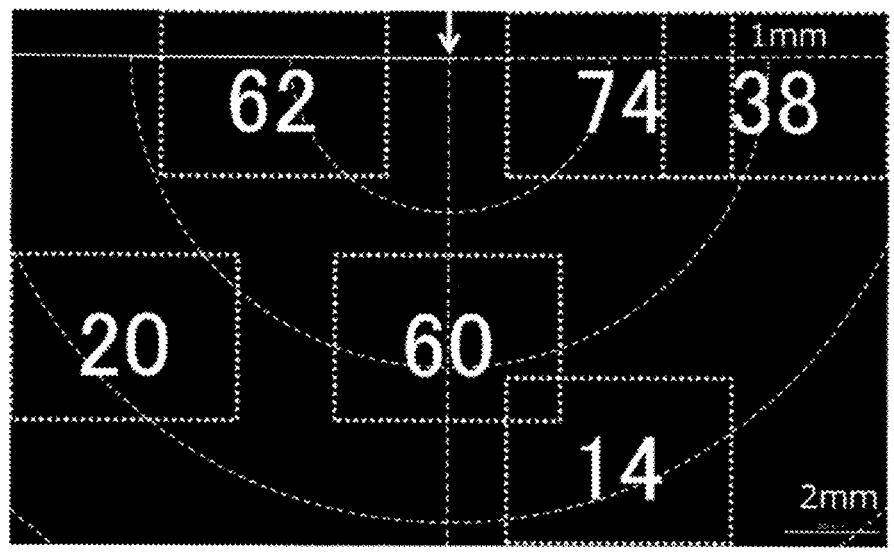
Figures 3, 17:
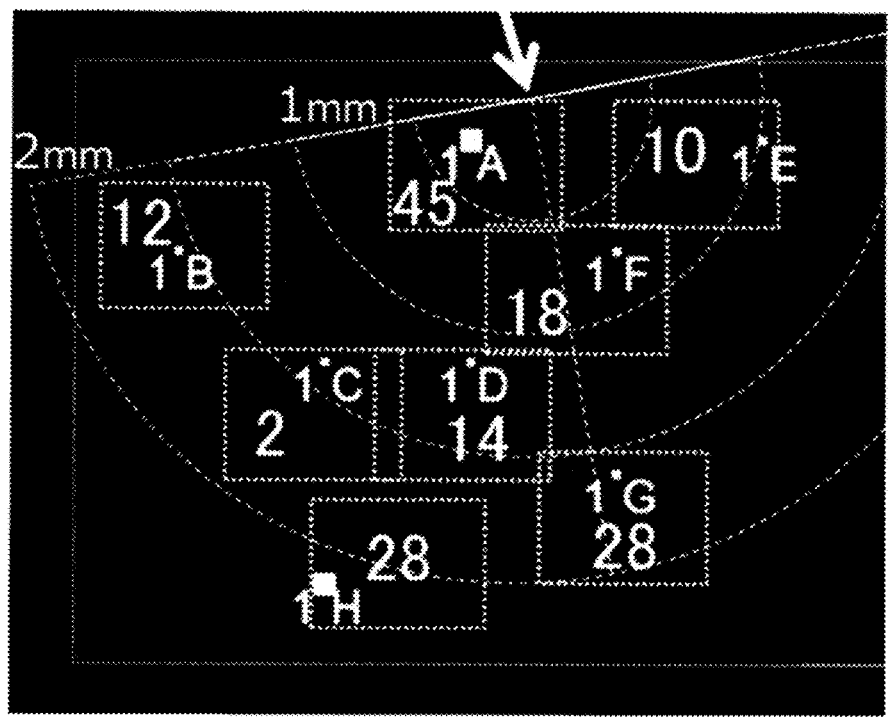
Figures 4, 17:
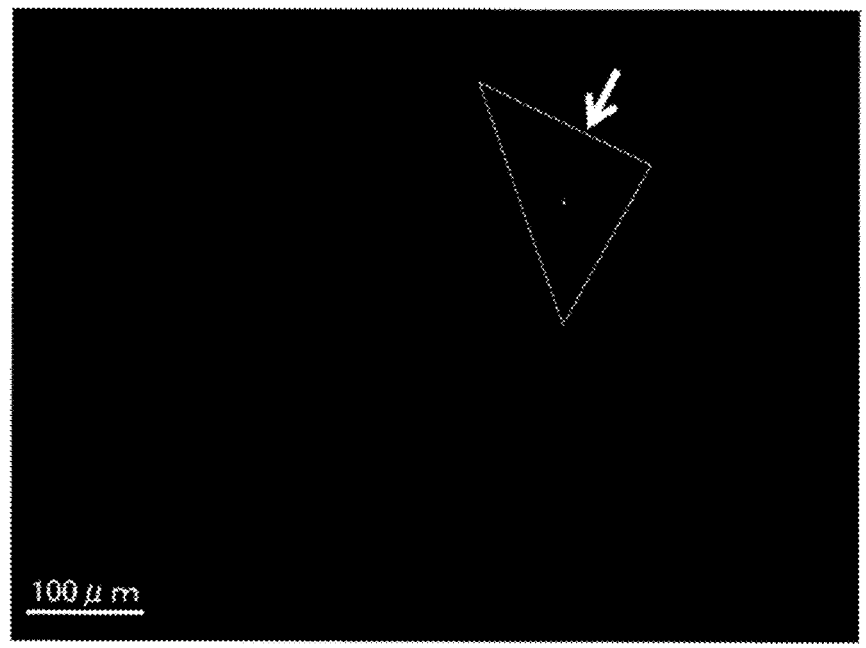
Figures 5, 17:
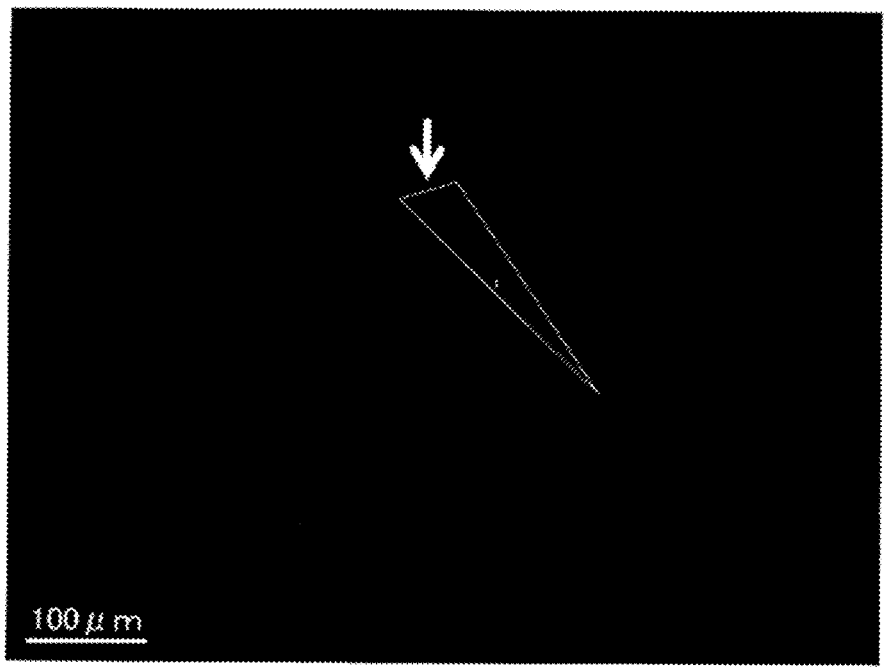
Figures 6, 17:
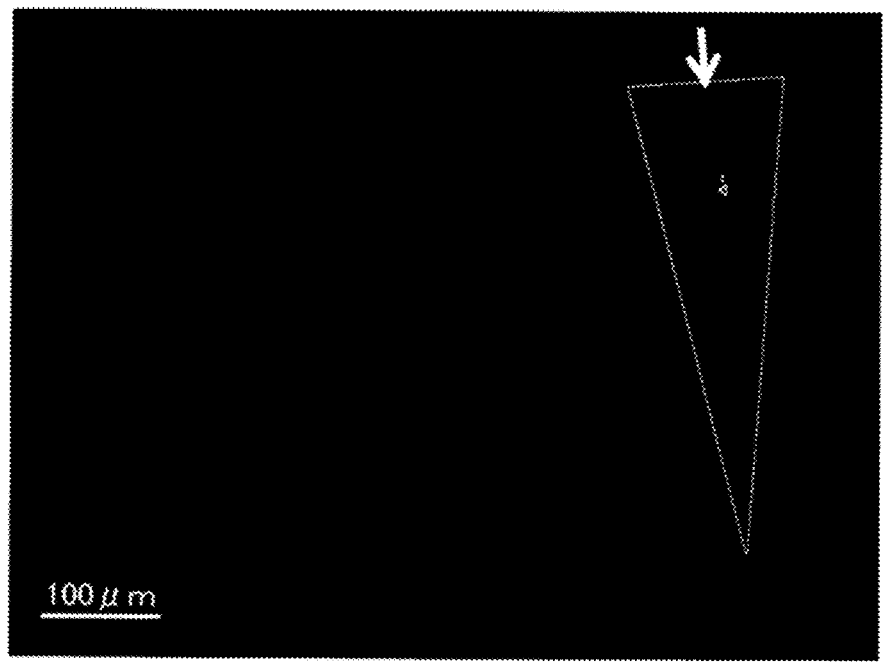

Immediately after injection, the skin was collected and frozen with dry ice in an OCT compound (embedding agent for preparing a frozen tissue section (Tissue-Tek O.C.T. Compound), commercially available from Sakura Finetek Japan Co., Ltd.). The cross section of the injection part was sliced to a thickness of 6 μm using a cryostat (commercially available from Leica Biosystems), and sealed with a DAPI-containing encapsulant. The prepared sample was fluorescently observed under an all-in-one fluorescence microscope (Z-x700, commercially available from Keyence Corporation), and a Cy3 red fluorescence image and a DAPI blue fluorescence image with a thickness of 0.1 to 0.4 μm were acquired. In order to obtain the injection distribution in the injection area, images in a plurality of fields of view were acquired. The results are shown in FIG. 17-1. Here, concentric circles drawn by dashed lines with the text "1 mm" and "2 mm" are concentric circles centered on the injection port. The white arrow indicates the injection port.

The proportion of the number of cells into which DNA was directly injected was calculated using a hybrid cell count function as follows. That is, for cells in each analysis target area (each area surrounded by the white dashed line in FIG. 17-1), cells in which a purple fluorescence area in which a blue fluorescence overlapped a red fluorescence was at least 50% of the area of cells were defined as cells into which DNA was directly injected, and the number of cells was counted (this is referred to as the number of cells A). On the other hand, the total number of cells in each analysis target area was counted using the number of cell nuclei as an index (this is referred to as the number of cells B). The numerical value described in each analysis target area in FIG. 17-1 is a ratio of the number of cells A to the number of cells B. Here, the epidermis and hair follicles in which almost no Cy3 red fluorescence was observed were excluded from the analysis target.

Figure 4:
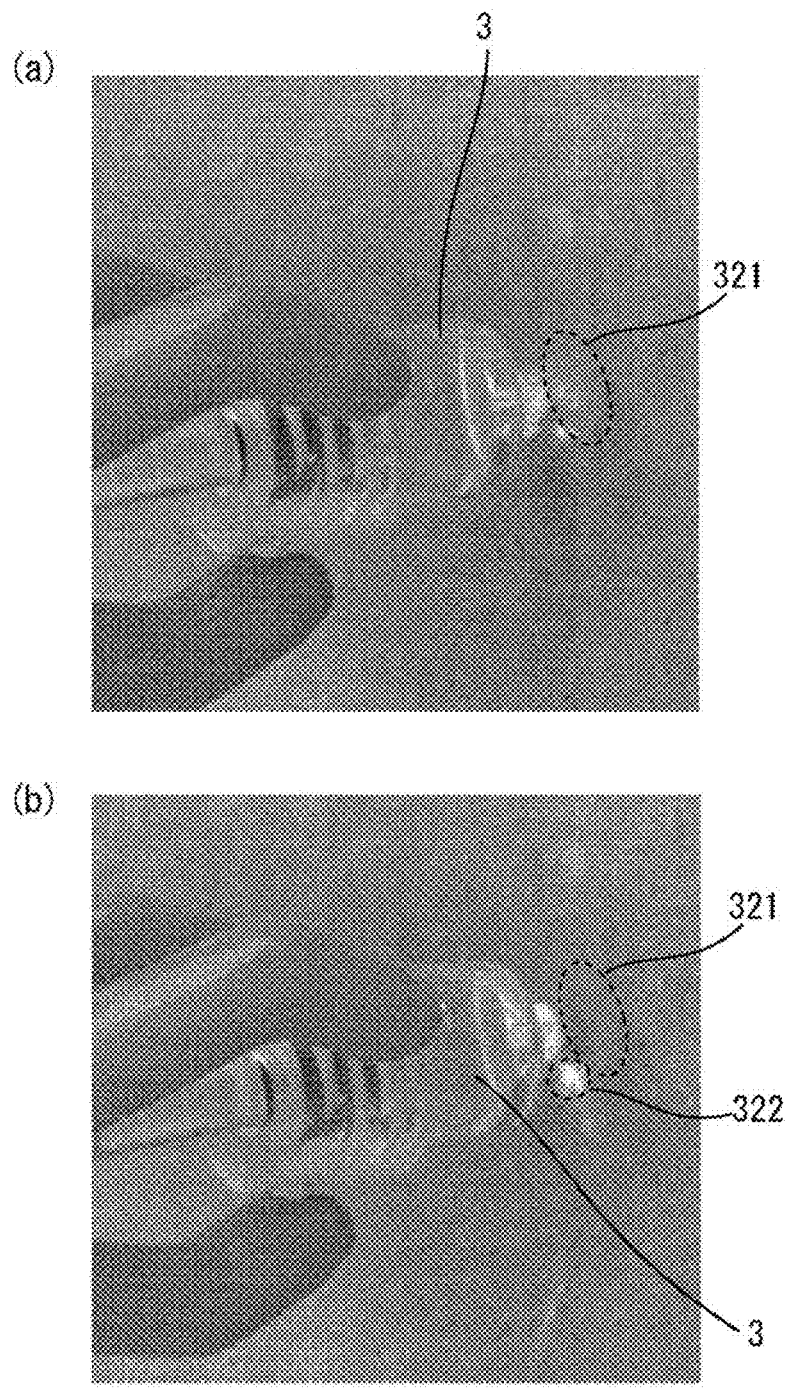

In addition, FIG. 17-4 shows an image near the injection port, which is an image for evaluating the degree of damage to the tissues near the injection port due to the injection of the DNA solution. The damaged part is a part surrounded by the white line in each drawing.

Example 2-2

The procedure was performed in the same manner as in Example 2-1 except that 55 mg of ZPP was used. The results are shown in FIG. 17-2. In addition, FIG. 17-5 shows an image near the injection port.

Comparative Example 2-1

The procedure was performed according to the instruction manual in the same manner as in Example 2-1 except that Biojector 2000 used in Comparative Example 1-1 was used, the solution was replaced with 70 μL of a solution containing Cy3-labled plasmid V7905. The results are shown in FIG. 17-3. In addition, FIG. 17-6 shows an image near the injection port.

From FIG. 17-1, FIG. 17-2, and FIG. 17-3, in Example 2-1, and Example 2-2, compared to Comparative Example 2-1, the proportion of DNA directly injected into cell nuclei of cells in a wide range from the injection port was significantly higher.

In addition, from FIG. 17-4, FIG. 17-5, and FIG. 17-6, in Example 2-1 and Example 2-2, compared to Comparative Example 2-1, damage to the tissues near the injection port was significantly little. Specifically, the area of the damaged part was $1.3 \times 10^4$ μm$^2$ in Example 2-1, $5.2 \times 10^3$ μm$^2$ in Example 2-2, but $2.7 \times 10^4$ μm$^2$ in Comparative Example 1-1.

REFERENCE SIGNS LIST

1 Injection syringe
3 Container part
20 Control device
21 First emission device
22 Second emission device
30 High speed camera
31 Flow path
31*a* Ejection port
31*b* Nozzle part
32 Tip surface
33*a* First outer peripheral surface
33*b* Second outer peripheral surface
33*c* Third outer peripheral surface
34 Storage space
35 Reflective member
38 Reflective layer
40 Power supply device
51 Object
101 Injection syringe
102 Housing
103 Syringe part
104 Plunger
105 Piston
106 Injection syringe main body
107 Drive unit
108 Button
109 Battery
110 Injection syringe assembly
131 Nozzle part
131*a* Ejection port
132 Filling chamber
171 Igniter

The invention claimed is:

1. A measurement system measuring a behavior of an ejection liquid, which is ejected into an object from an ejection device, within the object, the system comprising:
    a container part which includes a storage space, in which the ejection liquid is stored, and a flow path, through which the storage space communicates with an ejection port through which the ejection liquid is ejected to the outside, the container part being formed of a resin material;
    an imaging device which is disposed to image, across the object, a tip surface of the container part having the ejection port formed therein and positioned with respect to the object from a backside of the object in a predetermined state in which the ejection port is positioned from a front side of the object; and
    a first emission device configured to emit first near infrared light to the tip surface,
    wherein the first emission device is configured to emit the first near infrared light to the tip surface from the back side of the object, and an emission angle of the first near infrared light with respect to the tip surface is set such that light reflected at the tip surface is directed toward the imaging device, and
    wherein a tip side reflective layer configured to reflect a part of the first near infrared light emitted from the back side of the object is formed between the tip surface of the container part in the predetermined state and the object.

2. The measurement system according to claim 1, further comprising a second emission device configured to emit, from the front side of the object, second near infrared light that enters an outer peripheral surface of the container part, which is not in contact with the object in the predetermined state, and in which an angle of incidence of the second near infrared light on the outer peripheral surface is set such that the second near infrared light entering the container part passes through the container part and is directed toward the tip surface.

3. The measurement system according to claim 2, wherein, in the container part, in a predetermined area which is at least a part of the outer peripheral surface from a light entry position, at which the second near infrared light enters, to an end on the tip surface side, an outer peripheral side reflective member configured to reflect the second near infrared light that has passed through the container part from the light entry position and has reached the predetermined area to the container part is provided.

4. The measurement system according to claim 1, wherein the first emission device is configured to emit the first near infrared light per frame of the imaging device as pulsed light that blinks at a predetermined exposure time.

5. The measurement system according to claim 2, wherein the second emission device is configured to emit the second near infrared light per frame of the imaging device as pulsed light that blinks at a predetermined exposure time.

6. The measurement system according to claim 1, wherein the imaging device has an imaging speed of at least 1,000 fps (frame per second).

7. The measurement system according to claim 1, wherein the imaging device has an imaging speed of at least 10,000 fps (frame per second).

8. A method of measuring a behavior of an ejection liquid, which is ejected into an object from an ejection device, within the object, the method comprising:
   preparing the ejection device in which a container part is mounted, which includes a storage space, in which the ejection liquid is stored, and a flow path, through which the storage space communicates with an ejection port through which the ejection liquid is ejected to the outside, the container part being formed of a resin material;
   disposing an imaging device configured to image, across the object, a tip surface of the container part having the ejection port formed therein and positioned with respect to the object from a back side of the object in a predetermined state in which the ejection port is positioned from a front side of the object;
   emitting first near infrared light from a first emission device to the tip surface; and
   imaging the ejection liquid ejected from the ejection device by the imaging device when the first near infrared light is emitted by the first emission device,
   wherein the first emission device is configured to emit, from the front side of the object, the first near infrared light that enters an outer peripheral surface of the container part, which is not in contact with the object in the predetermined state, and in which an angle of incidence of the first near infrared light on the outer peripheral surface is set such that the first near infrared light entering the container part passes through the container part and is directed toward the tip surface, and the light is emitted to the tip surface.

9. A measurement system measuring a behavior of an ejection liquid, which is ejected into an object from an ejection device, within the object, the system comprising:
   a container part which includes a storage space, in which the ejection liquid is stored, and a flow path, through which the storage space communicates with an ejection port through which the ejection liquid is ejected to the outside, the container part being formed of a resin material;
   an imaging device which is disposed to image, across the object, a tip surface of the container part having the ejection port formed therein and positioned with respect to the object from a backside of the object in a predetermined state in which the ejection port is positioned from a front side of the object; and
   a first emission device configured to emit first near infrared light to the tip surface,
   wherein the first emission device is configured to emit, from the front side of the object, the first near infrared light that enters an outer peripheral surface of the container part, which is not in contact with the object in the predetermined state, and in which an angle of incidence of the first near infrared light on the outer peripheral surface is set such that the first near infrared light entering the container part passes through the container part and is directed toward the tip surface, and the light is emitted to the tip surface.

10. The measurement system according to claim 9, wherein, in the container part, in a predetermined area which is at least a part of the outer peripheral surface from a light entry position, at which the first near infrared light enters, to an end on the tip surface side, an outer peripheral side reflective member configured to reflect the first near infrared light that has passed through the container part from the light entry position and has reached the predetermined area to the container part is provided.

* * * * *